United States Patent
Pratt et al.

(10) Patent No.: US 10,323,017 B2
(45) Date of Patent: Jun. 18, 2019

(54) ANTIOXIDANTS AND METHODS TO MAXIMIZE PERFORMANCE

(71) Applicants: University of Ottawa, Ottawa (CA); Alma Mater Studiorum—Universita di Bologna, Bologna (IT)

(72) Inventors: Derek A. Pratt, Ottawa (CA); Ronak Mayankbhai Shah, Ottawa (CA); Evan Anthony Haidasz, Kingston (CA); Luca Valgimigli, Bologna (IT)

(73) Assignees: Alma Mater Studiorum—Universita di Bologna, Bologna (IT); University of Ottawa, Ottawa, Ontario (CA)

( * ) Notice: Subject to any disclaimer, the term of this patent is extended or adjusted under 35 U.S.C. 154(b) by 0 days.

(21) Appl. No.: 15/548,512

(22) PCT Filed: Feb. 5, 2016

(86) PCT No.: PCT/CA2016/050107
§ 371 (c)(1),
(2) Date: Aug. 3, 2017

(87) PCT Pub. No.: WO2016/123717
PCT Pub. Date: Aug. 11, 2016

(65) Prior Publication Data
US 2018/0022729 A1 Jan. 25, 2018

Related U.S. Application Data

(60) Provisional application No. 62/112,886, filed on Feb. 6, 2015.

(51) Int. Cl.
| | | |
|---|---|---|
| C07D 401/12 | (2006.01) | |
| C09D 7/40 | (2018.01) | |
| C07D 213/74 | (2006.01) | |
| C07D 239/42 | (2006.01) | |
| C07D 239/48 | (2006.01) | |
| C10M 133/40 | (2006.01) | |
| C09D 11/00 | (2014.01) | |
| C09K 15/30 | (2006.01) | |
| C09J 11/06 | (2006.01) | |
| C08K 5/3432 | (2006.01) | |
| C08K 5/3462 | (2006.01) | |
| A61K 8/49 | (2006.01) | |
| A61Q 19/00 | (2006.01) | |
| C10M 141/06 | (2006.01) | |
| C10L 1/10 | (2006.01) | |
| C10L 1/12 | (2006.01) | |
| C10L 1/232 | (2006.01) | |
| C10L 10/00 | (2006.01) | |
| C09K 15/18 | (2006.01) | |
| C08K 5/34 | (2006.01) | |

(52) U.S. Cl.
CPC .......... *C07D 401/12* (2013.01); *A61K 8/4926* (2013.01); *A61K 8/4953* (2013.01); *A61Q 19/00* (2013.01); *C07D 213/74* (2013.01); *C07D 239/42* (2013.01); *C07D 239/48* (2013.01); *C08K 5/3432* (2013.01); *C08K 5/3462* (2013.01); *C09D 7/40* (2018.01); *C09D 11/00* (2013.01); *C09J 11/06* (2013.01); *C09K 15/18* (2013.01); *C09K 15/30* (2013.01); *C10L 1/106* (2013.01); *C10L 1/1233* (2013.01); *C10L 1/232* (2013.01); *C10L 10/00* (2013.01); *C10M 133/40* (2013.01); *C10M 141/06* (2013.01); *A61K 2800/10* (2013.01); *A61K 2800/522* (2013.01); *C08K 5/34* (2013.01); *C10L 2200/0476* (2013.01); *C10L 2230/08* (2013.01); *C10L 2270/026* (2013.01); *C10M 2201/062* (2013.01); *C10M 2207/026* (2013.01); *C10M 2207/401* (2013.01); *C10M 2207/402* (2013.01); *C10M 2215/064* (2013.01); *C10M 2215/221* (2013.01); *C10N 2210/01* (2013.01); *C10N 2210/02* (2013.01); *C10N 2230/10* (2013.01); *C10N 2240/04* (2013.01); *C10N 2240/042* (2013.01); *C10N 2240/08* (2013.01); *C10N 2240/10* (2013.01)

(58) Field of Classification Search
CPC .................................................. C07D 401/12
USPC ......................................................... 546/23
See application file for complete search history.

(56) References Cited

U.S. PATENT DOCUMENTS

| | | | |
|---|---|---|---|
| 3,655,559 A | 4/1972 | Holt | |
| 9,738,606 B2 * | 8/2017 | Pratt | .................... C07D 213/74 |
| 2014/0206585 A1 * | 7/2014 | Pratt | .................... C07D 213/74 |
| | | | 508/266 |

FOREIGN PATENT DOCUMENTS

CA 2871190 12/2012

OTHER PUBLICATIONS

Hanthorn, Journal of Organic Chemistry (2012), 77(16), 6895-6907.*
Pratt ,Journal of the American Chemical Society (2002), 124(37), 11085-11092.*
Pratt, Acc. Chem. Res. 2004, 37, 334.*
International Search Report for International Application No. PCT/CA2016/050107 dated May 2, 2016.

(Continued)

*Primary Examiner* — Nizal S Chandrakumar
(74) *Attorney, Agent, or Firm* — Lowenstein Sandler LLP; Angela Lyon

(57) ABSTRACT

A method of preventing or reducing the level of degradation of an organic substrate is described, wherein a composition is formed that includes the organic substrate together with an effective amount of a sacrificial base and a diarylamine antioxidant.

15 Claims, 23 Drawing Sheets

(56) References Cited

OTHER PUBLICATIONS

Written Opinion for International Application No. PCT/CA2016/050107 dated May 2, 2016.
Hanthorn et al., "Inc. of Ring Nitrogens into Diphenylamine Antioxidants: Striking a Balance between Reactivity and Stability" J. Am. Chem. Soc. Feb. 2012, 34, 8306-8309.

* cited by examiner

| Antioxidant Compound No. | Structural Formula |
|---|---|
| 1: $R_1 = C_4H_9$, $R_2 = C_6H_{13}$ <br> 26: $R_1 = CH_2CH_3$, $R_2 = CH_3$ | 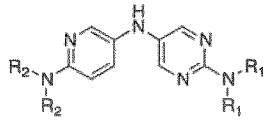 <br> $k_1(37°C) = 3.1 \times 10^7 \, M^{-1}s^{-1}$, $E^0 = 0.50V$ |
| 2: $R = C_4H_9$ | 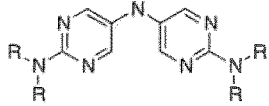 <br> $k_1(37°C) = 1.8 \times 10^7 \, M^{-1}s^{-1}$, $E^0 = 0.65V$ |
| 3: $R = C_6H_{13}$ <br> 24: $R = CH_3$ | 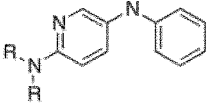 <br> $k_1(37°C) = 1.1 \times 10^7 \, M^{-1}s^{-1}$, $E^0 = 0.60V$ |
| 4: $R = C_6H_{13}$ <br> 22: $R = CH_3$ | 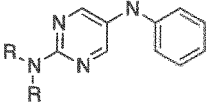 <br> $k_1(37°C) = 3.0 \times 10^6 \, M^{-1}s^{-1}$, $E^0 = 0.81V$ |
| 5: $R_1 = C_7H_{15}$, $R_2 = C_4H_9$ | 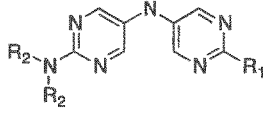 <br> $k_1(37°C) = 2.4 \times 10^6 \, M^{-1}s^{-1}$, $E^0 = 0.84V$ |
| 6: $R = C_7H_{15}$ | 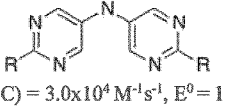 <br> $k_1(37°C) = 3.0 \times 10^4 \, M^{-1}s^{-1}$, $E^0 = 1.55V$ |
| 7: $R = C_8H_{17}$ <br> 21: $R = CH_3$ | 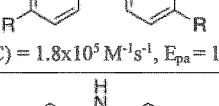 <br> $k_1(37°C) = 1.8 \times 10^5 \, M^{-1}s^{-1}$, $E_{pa} = 1.02V$ |
| 20: $R = C_8H_{17}$ <br> 23: $R = CH_3$ | 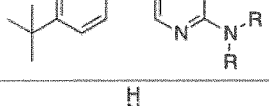 |
| 25: $R = CH_3$ |  |

Fig. 1

ANTIOXIDANTS AND METHODS TO MAXIMIZE PERFORMANCE

RELATED APPLICATION

This application claims the benefit of the filing date of U.S. Provisional Patent Application No. 62/112,886 filed on Feb. 6, 2015, the contents of which are incorporated herein by reference in their entirety.

FIELD OF THE INVENTION

This invention relates to substituted heteroaromatic diarylamine compounds which are particularly useful as antioxidants.

BACKGROUND OF THE INVENTION

Antioxidants are compounds that can retard oxidation, and thus are useful as additives to increase the stability and lifespan of one or more organic substrates that are subject to oxidative degradation. Such degradation may occur under ambient conditions or may be induced by heat and/or light. Antioxidants can be useful as protective additives in engine oils, automatic transmission fluids, industrial utility grade oils, compressor oils, gear and hydraulic oils, biodiesels, plastics, rubber and rubber like substances, unsaturated monomers, elastomers, adhesives, cosmetics preparations, coatings, dyes, inks, and pharmaceutical preparations. Antioxidants are also useful as additives present during the processing or synthesis of many organic substrates, for example as additives during polymerization, because of the ability of the antioxidant to scavenge free radicals, and thus improve the yield, stability and longevity of the desired resulting product.

Antioxidants are commonly added to organic substrates such as combustion engine lubricating oils, to assist in reducing unwanted oxidation, and increasing performance standards. Combustion engine lubricants oxidize readily at the high operating temperatures of an engine, and in turn, have diminished lubricating capacity as the viscosity of the lubricant increases, and the oxidation products accumulate to form deposits, which in turn leads to greater wear on engine parts.

The chemical mechanism of a typical autoxidation reaction (a free radical chain reaction) which benefits from the addition of an antioxidant is shown in Chart 1 below for a generic hydrocarbon R—H.

The initiation reaction is typically any reaction that gives rise to radicals, but is often the homolytic decomposition of a hydroperoxide at high temperatures, or the dissociative electron transfer to a hydroperoxide in the presence of low valent metal ions (e.g. $Fe^{2+}$, $Cu^{1+}$) or other good reductants.

A key strategy in decreasing the rate at which an organic substrate oxidizes is the addition of small quantities of antioxidant compounds which trap the intermediate radicals that carry on the oxidation process. These antioxidants should be compatible with the organic product of interest and/or the formulation thereof, and should themselves be robust and stable.

One of the common types of compounds used as an antioxidant additive are compounds based on diphenylamines.

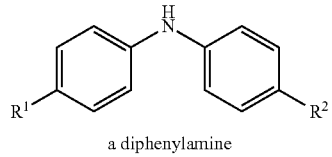

a diphenylamine

Diphenylamines with antioxidant activity are well known in the art. See for example, U.S. Pat. Nos. 2,180,936, 3,655,559; 3,944,492; 5,750,787; 6,315,925, and 2,530,769, all of which, without adopting any definitions as found therein, are incorporated herein by reference.

For example, U.S. Pat. No. 3,655,559 discloses alkylated diphenylamines useful as additives to lubricating oils. U.S. Pat. No. 2,180,936 describes use of substituted diphenylamines in the manufacture of rubber and rubber like compounds to impart age-resisting qualities as a result of the antioxidant capabilities of these compounds.

Other diphenylamines are also well known in the art. See for example U.S. Pat. No. 3,944,492 which discloses use of derivatives of diphenylamines and phenylnapthylamines as antioxidants and U.S. Pat. No. 5,750,787 which describes octyl-substituted diphenylamines.

While substituted diphenylamine antioxidants are used commercially as the additives of choice at high temperatures, the radical trapping activities of these compounds are only modest at ambient temperatures due to relatively low inhibition rate constants ($k_{inh}$, see Chart 2) that is the rate controlling parameter in inhibited autoxidations.

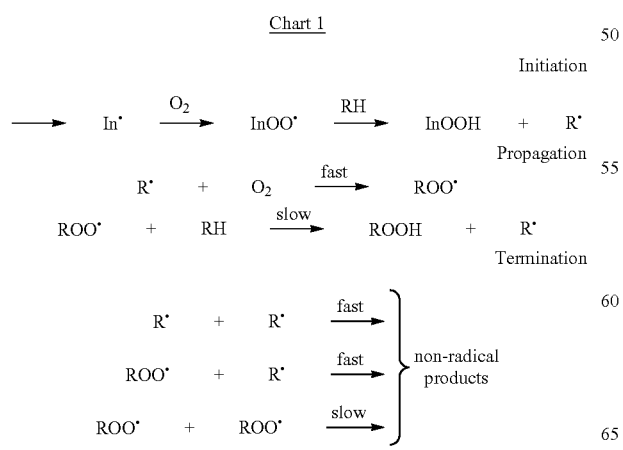

Chart 1

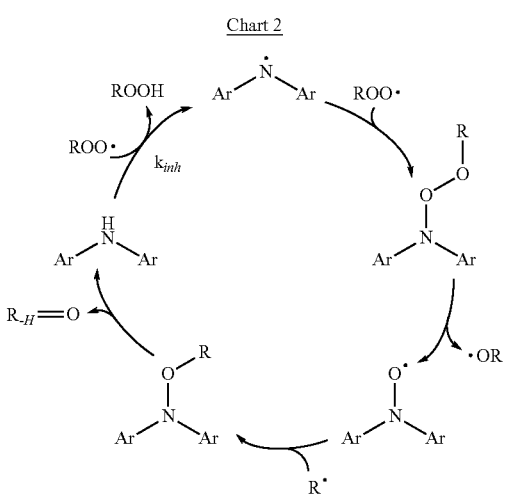

Chart 2

At higher temperatures, these compounds become more effective, since catalytic activities, which are not fully understood but are ascribed to the intervention of nitroxides, become relevant (Korcek, S., et al., *ASLE Transactions*, Vol. 19, No. 2, 1975 pp. 83-94 and Jensen, R. K., et al., *J. Org. Chem.* 1995, 60, 5396-5400).

Efforts to design diphenylamine-based antioxidants with improved reactivity while maintaining stability have met with little success, since the candidates are often unstable in air, making them more likely to act as pro-oxidants and complicating their preparation, handling and storage.

As such, it would be advantageous to have antioxidant compounds that are stable with longevity and utility, while still maintaining their reactivity. The ability to be stable at both ambient temperature and elevated temperatures would also be beneficial.

SUMMARY OF THE INVENTION

It is an object of the present invention to maximize performance of diarylamine antioxidants. An aspect of the invention provides a method of preventing or reducing the level of degradation of an organic substrate, the method includes adding to a composition that comprises an organic substrate, effective amounts of a base and an antioxidant, wherein the antioxidant is a diaryl amine that includes at least one N-heteroaryl moiety, and having at least one electron donating group as a substituent on an aryl ring carbon. In an embodiment of this aspect the organic substrate is engine oil, automatic transmission fluid, crank case lubricant, industrial utility grade oil, compressor oil, gear oil, hydraulic oil, biodiesel, plastic, rubber, rubber-like substance, unsaturated monomer, elastomer, adhesive, cosmetic preparation, coating, dye, ink, pharmaceutical preparation, or combustion engine lubricating oil. In another embodiment of this aspect, the base is 2,4,6-tri-tert-butylpyridine (TTBP), cesium carbonate, tert-alkylated primary amine, PRIMENE™ 81-R, a metal oxide, metal hydroxide, or metal carbonate, wherein the metal is sodium, potassium, magnesium, calcium, or barium.

In another embodiment of this aspect, the antioxidant is a compound of Formula I, IA, IB, or II, or any salt thereof, Formula I

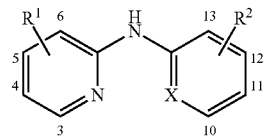

Formula IA

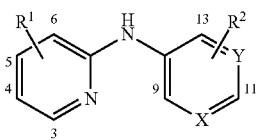

Formula IB

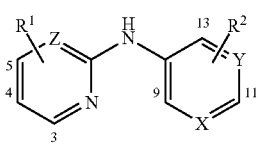

Formula II

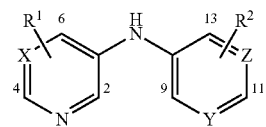

wherein each of X, Y and Z are independently a carbon or nitrogen atom; and wherein $R^1$ and $R^2$ are each independently a hydrogen or an electron donating group, but are not both hydrogen, and wherein $R^1$ and $R^2$ are each bonded to a carbon atom within their respective aryl ring. In another embodiment of this aspect, the compound of Formula I, IA, IB, or II, is compound 1, 2, 3, 4, 5, 6, 20, 22-26, or any salt thereof

1

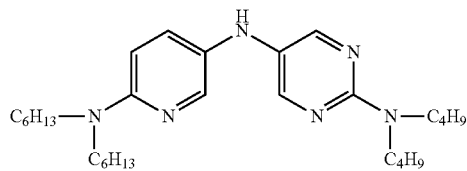

2

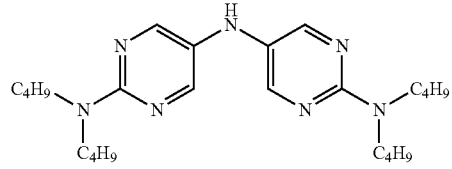

3

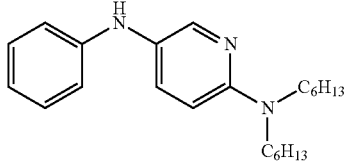

4

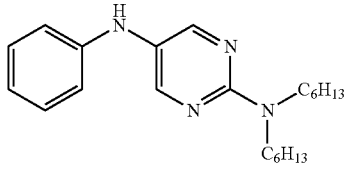

5

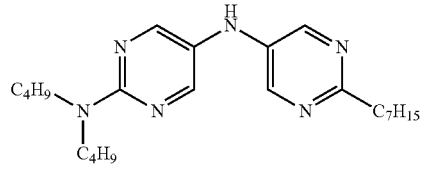

6

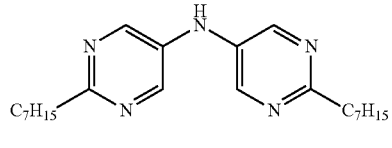

20

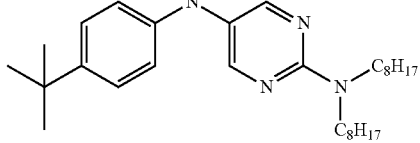

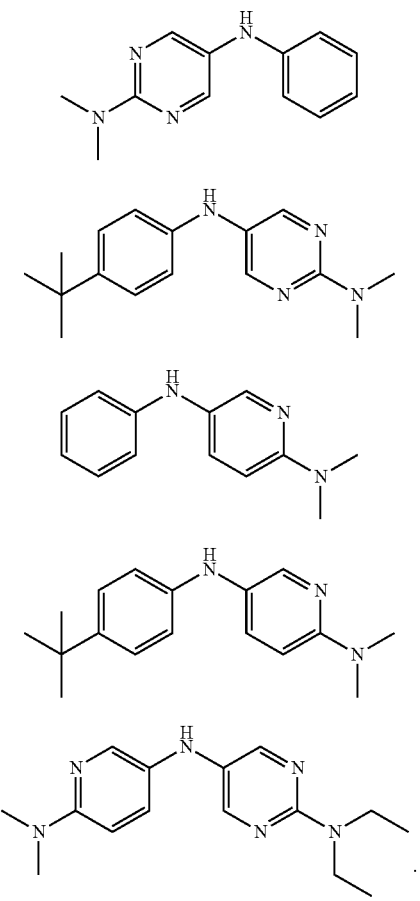

In another aspect, the invention provides a composition that includes a base and an antioxidant, wherein the antioxidant is a diaryl amine that includes at least one N-heteroaryl moiety, and having at least one electron donating group as a substituent on an aryl ring carbon. In another embodiment of this aspect, the antioxidant is a compound of Formula I, IA, IB, or II, or any salt thereof, as shown above. In yet another embodiment of this aspect, the electron donating group is an amine or a tert-butyl group. In another embodiment of this aspect, the amine is a dialkylamine. In another embodiment of this aspect, the compound of Formula I, IA, IB, or II, is compound 1, 2, 3, 4, 5, 6, 20, 22-26 as shown above, or any salt thereof. In another embodiment of this aspect, the organic substrate is selected from the group consisting of lubricants, biofuels, plastics, rubbers, polymers, elastomers, cosmetic preparations, coatings, dyes, inks, pharmaceutical preparations, food preparations and adhesives. In another embodiment of this aspect, the organic substrate is a lubricant, and the compound(s) are present in an amount of about 0.01 to about 6 weight percent of said lubricant. In another embodiment of this aspect, the organic substrate is a lubricant, and the compound(s) are present in an amount of about 0.03 to about 2.5 weight percent of said lubricant. In yet another embodiment of this aspect, the composition further comprises one or more additional antioxidants. In another embodiment of this aspect, the additional antioxidant is a sterically hindered phenol. In another embodiment of this aspect, the one or more additional antioxidants is selected from the group consisting of traditional anti-oxidants, anti-wear agents, zinc salts, anti-deposition agents, hydrolytic stabilizers, friction modifiers, seal swell agents, anti-rust agents, foam suppressing agents, and pour point depressants.

In another aspect, the invention provides use of a composition of any one of the above embodiments. In another embodiment of this aspect, the composition comprises one or more monomers which are to be used in the synthesis of a polymer.

In yet another aspect, the invention provides a kit that includes a base and an antioxidant of Formula I, IA, IB, or II, or any salt thereof, as shown above, and instructions for use to scavenge at least one free radical species from within a composition containing or used to synthesize an organic substrate, thus improving the stability and/or yield of the organic substrate. In an embodiment of this aspect, the kit includes a compound of Formula I, IA, IB, or II that is a compound 1, 2, 3, 4, 5, 6, 20, 22-26 as shown above, or any salt thereof.

In another aspect the invention provides, a method of improving the stability and/or yield of an organic substrate, the method includes adding to a composition comprising or resulting in said organic substrate, an effective amount of (i) a base, and (ii) an antioxidant of Formula I, IA, IB, or II as shown above, or any salt thereof.

In certain embodiments of these aspects, the organic substrate is engine oil, automatic transmission fluid, crank case lubricant, industrial utility grade oil, compressor oil, gear oil, hydraulic oil, biodiesel, plastic, rubber, rubber-like substance, unsaturated monomer, elastomer, adhesive, cosmetic preparation, coating, dye, ink, pharmaceutical preparation, or combustion engine lubricating oil. In some embodiments, the organic substrate is an oil, fat and/or wax, including those used in the cosmetic and/or pharmaceutical industry, including those oils, fats and/or waxes comprising esters of saturated and/or monounsaturated and/or polyunsaturated fatty acids, including unsaponifiable fractions obtained from such oils, fats and waxes. Also included are dietary oils and fats, and oils and fats used in manufacturing of food or food ingredients. Included also are oils, fats and waxes such as almond oil, apricot oil, castor oil, corn oil, macadamia nut oil, olive oil, sesame oil, soybean oil, fish oil, bird oil, jojoba oil, bees wax, lanolin, oleic acid, linoleic acid, linolenic acid, and the like, as well as their esters.

Other aspects and features of the present invention will become apparent to those ordinarily skilled in the art, upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 1 shows structural formulas for representative diarylamines and their $k_1$ (rate constant, see equation 1 herein) and $E°$ (standard reduction potential) properties.

DETAILED DESCRIPTION

Definitions

Figure 2A:
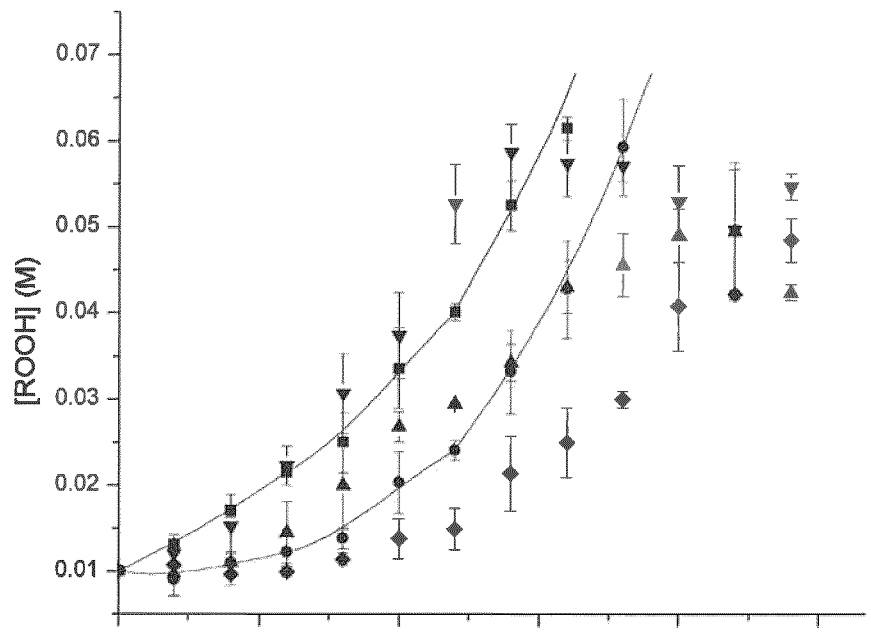
FIG. 2A shows data pertaining to hydroperoxide formation in the autoxidation of hexadecane at 160° C. initiated by 10 mM tetralin hydroperoxide (■) in the presence of 40 μM of 1 (▼), 2 (♦), 3 (▲), or 7 (●).

As used herein, "aliphatic" refers to hydrocarbon moieties that are linear, branched or cyclic, may be alkyl, alkenyl or alkynyl, and may be substituted or unsubstituted.

The term "aromatic hydrocarbon", as used herein, includes hydrocarbons containing at least one aromatic ring.

The terms "aryl", "aryl ring" and "aryl group", as used herein, mean a moiety including a substituted or unsubstituted aromatic ring, including heteroaryl moieties and moieties with more than one conjugated aromatic ring; optionally such moiety may also include one or more non-aromatic ring. The terms "aryl", "aryl ring" and "aryl group" also include heteroaryl groups, wherein at least one ring atom is a non-carbon atom (e.g., nitrogen (N)).

Accordingly, as used herein, "heteroaryl" means a moiety including a substituted or unsubstituted aromatic ring or ring system having from 3 to 20, or 4 to 10 carbon atoms and at least one heteroatom in one or more conjugated aromatic rings. As used herein, "heteroatom" refers to non-carbon and non-hydrogen atoms, such as, for example, O, S, and N. Examples of heteroaryl moieties include pyridyl, bipyridyl, indolyl, thienyl, and quinolinyl.

The term "effective amount" herein refers to the amount of compound (or compounds) which is added to an organic substrate so as to provide activity. In some embodiments, the "effective amount" is an amount of compound(s) sufficient to reduce the level of degradation of an organic substrate when compared to the level of degradation of the organic substrate in the absence of said compound(s). In some embodiments, the "effective amount" is an amount sufficient to enable the compound(s) to scavenge one or more free radicals existing, or formed within a composition. In some embodiments, the "effective amount" is an amount sufficient to enable the compound(s) to scavenge one or more free radicals during synthesis of an organic substrate.

The term "electron donating group" as used herein includes a hydrocarbon group, an alkoxy group ($OR^3$), an amine group, a monosubstituted amine ($NHR^4$), and a disubstituted amine ($NR^4R^5$). The electron-donating strength of the alkoxy or amine group comes largely from the lone pairs of electrons on the O and N atoms, respectively, such that each of $R^3$, $R^4$ and $R^5$ can be a hydrogen or a saturated or unsaturated branched or straight chain hydrocarbon moiety and/or may include one or more cycloaliphatic groups and/or one or more aromatic hydrocarbons, or a combination thereof, while not detracting from the electron donating characteristic of the alkoxy or amine group.

The term "cycloaliphatic" as used herein includes a saturated or unsaturated carbocyclic moiety comprising mono- or bicyclic rings. Cycloaliphatic includes a 3- to 7-membered saturated carbocyclic moiety. Examples of cycloaliphatic moieties include, but are not limited to, cyclopropyl, cyclobutyl, cyclopentyl, cyclohexyl, cycloheptyl, and the like, including partially unsaturated derivatives thereof such as cyclohexenyl, cyclopentenyl, and the like.

The term "hydrocarbon group", as used herein, includes a hydrocarbon containing between 1 to 24 carbons, and includes saturated or unsaturated, branched or straight chain hydrocarbon moieties, including aliphatic moieties and/or one or more cycloaliphatic groups and/or one or more aromatic hydrocarbons, or a combination thereof.

The term "tetralin hydroperoxide" refers to 1-hydroperoxy-1,2,3,4-tetrahydronaphthalene. It is an initiator of hydrocarbon autoxidation.

The term "degradation", as used herein, includes a process that benefits from the activity of antioxidants. Degradation includes damage that occurs as a result of oxidation and/or the activity of one or more free radicals.

The term "level of degradation", as used herein, refers to a qualitative, semi-qualitative, quantitative or semi-quantitative assessment of the amount and/or extent of damage resulting from degradation, including degradation caused by oxidation and/or the activity of one or more free radicals. The assessment can include functional measurements of the activity of the substance for which the level of degradation is being assessed.

The term "lubricant", as used herein, includes a substance (often a liquid) that can be introduced between two moving surfaces to reduce the friction between them.

The term "organic substrate", as used herein, includes a non-living carbon based compound or composition and includes those carbon based compounds or compositions that can be subjected to oxidative degradation. Such degradation may occur under ambient conditions or can be induced by heat and/or light, and can benefit from the addition of an antioxidant. Organic substrates are also compounds that can benefit from a compound that can scavenge at least one free radical species and improve the yield, stability and/or longevity of the organic substrate, for example, a compound added during synthesis of a polymer to scavenge free radicals formed. Therefore, organic substrates include monomers, dimers, trimers and polymers including triglycerides, phospholipids, sphingolipids, and other lipids, which can benefit from the addition of one or more antioxidants able to scavenge free radicals. Included within the definition of organic substrates, although not intended to be limiting, are oils such as engine oils, automatic transmission fluids, industrial oils, compressor oils, gear and hydraulic oils, and the like. Also included are hydraulic fluids and fuels, biodiesels, plastics, rubber and rubber-like substances, unsaturated monomers, cosmetic preparations, coatings, dyes, inks, pharmaceutical preparations, elastomers, adhesives, and other hydrocarbon based polymers. Also included are oils, fats and waxes typically used in the cosmetic and/or pharmaceutical industry, including those oils, fats and/or waxes comprising esters of saturated and/or monounsaturated and/or polyunsaturated fatty acids, including unsaponifiable fractions obtained from such oils, fats and waxes. Also included are dietary oils and fats, and oils and fats used in manufacturing of food or food ingredients. Included also are oils, fats and waxes such as almond oil, apricot oil, castor oil, corn oil, macadamia nut oil, olive oil, sesame oil, soybean oil, fish oil, bird oil, jojoba oil, bees wax, lanolin, oleic acid, linoleic acid, linolenic acid, and the like, as well as their esters.

The term "salt" as used herein includes, for example, acid addition salts and base addition salts. Acid addition salts include salts wherein the diaryl amine of Formula I or Formula II remains protonated, for example at the heterocyclic nitrogen or the 'reactive' bridging nitrogen. Base addition salts include compounds of Formula I or Formula II resulting in deprotonated amine, as well as the amide form of the amine, which may be generated by treatment with a strong base, for example lithium diisopropylamide.

Embodiments

Substituted diarylamines that include at least one N-heteroaryl moiety and that have at least one electron withdrawing group substituent on an aryl carbon have been designed and their antioxidant activity has been quantified, see international patent application No. PCT/CA2012/000546, published as WO/2012/162818, now U.S. patent application Ser. No. 14/123,452, published as US 2014/0206585, and Canadian Patent Application No. 2,871,190.

Surprisingly, the presence of a base has been revealed to significantly improve performance of such compounds as antioxidants. Interestingly, the presence of base does not improve the performance of diphenyl amine, a commercially available antioxidant. Studies have been conducted to quantify the improvement of the antioxidant activity of N-heteroaryl compounds and these studies are described herein.

Any base is suitable for this role provided it is sacrificed and effectively neutralizes an acid before the acid has an opportunity to interfere with an antioxidant. Common metals can be used to make neutral or basic additives. Example of such common metals include sodium, potassium, magnesium, calcium, and barium. Calcium and magnesium find most extensive use as lubricant additives, with a preference for calcium due to its lower cost. Accordingly, bases can include metal oxides, hydroxides, and carbonates.

Diarylamine radical-trapping antioxidants ($Ar_2NH$) are key additives to many types of petroleum-derived products due to their high inherent reactivities to peroxyl radicals (Eq. 1) and the persistence of the resultant radicals to both $O_2$ and non-radical species. Instead, the diarylaminyl radicals react with another peroxyl radical to yield a nitroxide (Eq. 2), which can either react with a peroxyl radical on one of the aryl rings or combine with an alkyl radical to give an alkoxyamine (Eq. 3). Either way, a single molecule of $Ar_2NH$ inhibits the propagation of two autoxidative chain reactions and gives rise to an overall stoichiometry (or 'stoichiometric factor') of 2.

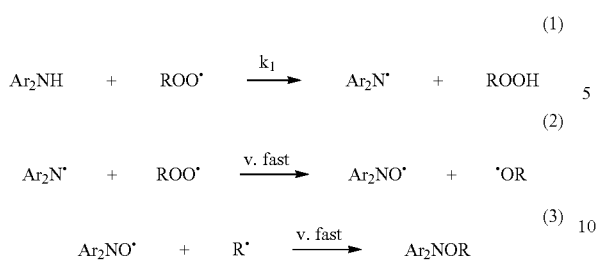

(1) $Ar_2NH + ROO^\bullet \xrightarrow{k_1} Ar_2N^\bullet + ROOH$ (2) $Ar_2N^\bullet + ROO^\bullet \xrightarrow{v.\ fast} Ar_2NO^\bullet + {}^\bullet OR$ (3) $Ar_2NO^\bullet + R^\bullet \xrightarrow{v.\ fast} Ar_2NOR$ At elevated temperatures, such as those to which engine lubricants are exposed and polymers are processed, much greater stoichiometric factors have been reported. For example, a remarkable stoichiometric factor of 52 was determined for a 4,4'-dialkyldiphenylamine in paraffin oil at 130° C., indicating that diphenylamines can trap several peroxyl radicals per molecule of amine. The apparent catalytic antioxidant behaviour of diphenylamines results from the regeneration of the diphenylamine from the N,N-diarylalkoxyamine (Eq. 4). This transformation, which occurs either by N—O dissociation and in-cage disproportionation or a retro-carbonyl-ene reaction depending on the structure of the aryl and alkyl moieties, is believed to underlie the unique efficacy of diphenylamine radical-trapping antioxidants in high-temperature applications.

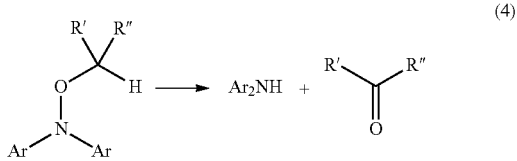

(4)

It has been shown that incorporation of nitrogen atoms into the aromatic rings of phenolic and diphenylamine radical-trapping antioxidants enables the design of compounds with outstanding reactivities toward peroxyl radicals (i.e. $\Delta H_1^\ddagger \approx 0$). Results of the reactivity of these heterocyclic diarylamine radical-trapping antioxidants at 160° C. have been shown; a temperature far more representative of their potential 'real world' applications, and at which the reaction in Eq. 4 may be expected to occur.

Antioxidants whose performance is enhanced by the presence of a base are compounds of general formulas I, IA, IB, and/or II, or any salt thereof, Formula I

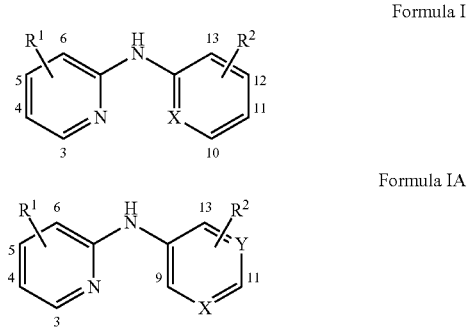

Formula IA

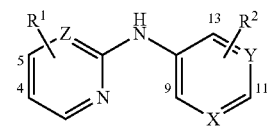

Formula IB

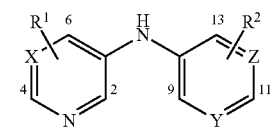

Formula II each of X, Y, and Z are independently a carbon or nitrogen atom, wherein $R^1$, and $R^2$ are each independently a hydrogen or an electron donating group, but are not both hydrogen, and wherein $R^1$ and $R^2$ are each bonded to a carbon atom within their respective aryl ring.

In some embodiments such compounds do not include $N^1,N_1$-dimethyl-$N^4$-(3-pyridyl)phenylenediamine, N-(3-pyridyl)-3-methylaniline, $N^1,N^1$-dimethyl-$N^4$-(3-pyridyl) phenylenediamine or N-(3-pyridyl)-3-methylaniline. In some embodiments such compounds are those of Formula II where X, Y, and Z are all carbons, $R^1$ is a hydrogen and $R^2$ is an electron donating group, but is not a methyl group or a dimethylamine.

In some embodiments of Formula I, Formula IA, Formula IB and/or Formula II, $R^2$ is a hydrogen and $R^1$ is an electron donating group. In some embodiments $R^1$ is a hydrogen and $R^2$ is an electron donating group. In some embodiments, both $R^1$ and $R^2$ are electron donating groups and the $R^1$ and $R^2$ electron donating groups are the same. In other embodiments both $R^1$ and $R^2$ are electron donating groups and the $R^1$ and $R^2$ electron donating groups are different. In some embodiments, at least one electron donating group is a hydrocarbon group. In some embodiments the hydrocarbon group is a saturated or unsaturated, branched or straight chain hydrocarbon moiety. In some embodiments, the hydrocarbon group is aliphatic. In some embodiments the hydrocarbon group is a saturated or unsaturated, branched or straight chain hydrocarbon moiety covalently linked to one or more aromatic hydrocarbons. In other embodiments, the hydrocarbon group is a saturated or unsaturated, branched or straight chain hydrocarbon moiety covalently linked to a cycloaliphatic group. In other embodiments the hydrocarbon group is a saturated or unsaturated, branched or straight chain hydrocarbon moiety covalently linked to one or more aromatic hydrocarbons and/or one or more cycloaliphatic groups. In yet other embodiments, $R^1$ and/or $R^2$ is one or more cycloaliphatic groups. In yet other embodiments, $R^1$ and/or $R^2$ is one or more aromatic hydrocarbons. In yet other embodiments, $R^1$ and/or $R^2$ is one or more cycloaliphatic groups covalently linked to one or more aromatic hydrocarbons (or vice versa). In yet other embodiments, $R^1$ is a hydrogen and $R^2$ is a hydrocarbon group which is not a methyl group. In yet other embodiments, $R^1$ is a hydrogen and $R^2$ is a hydrocarbon group which is not a dimethylamine group.

In some embodiments, such compounds of Formula I, Formula IA, Formula IB and/or Formula II, have an electron donating group that is an alkoxy group ($OR^3$). In some embodiments, the $R^3$ group is a hydrogen. In some embodiments the $R^3$ is a hydrocarbon group and in some embodiments is a saturated or unsaturated, branched or straight chain hydrocarbon moiety. In other embodiments $R^3$ is a saturated or unsaturated, branched or straight chain hydrocarbon moiety covalently linked to one or more aromatic hydrocarbons. In other embodiments, $R^3$ is a saturated or unsaturated, branched or straight chain hydrocarbon moiety covalently linked to a cycloaliphatic group. In other embodiments $R^3$ is a saturated or unsaturated, branched or straight chain hydrocarbon moiety covalently linked to one or more aromatic hydrocarbons and/or one or more cycloaliphatic groups. In yet other embodiments, $R^3$ is one or more cycloaliphatic groups. In yet other embodiments, $R^3$ is one or more aromatic hydrocarbons. In yet other embodiments, $R^3$ is one or more cycloaliphatic groups covalently linked to one or more aromatic hydrocarbons (or vice versa).

In some embodiments of Formula I, Formula IA, Formula IB and/or Formula II, at least one electron donating group is an amine group ($NR^4R^5$). In some embodiment $R^4$ and $R^5$ cannot both be hydrogen. In other embodiments $R^4$ is a hydrogen and $R^5$ is an electron donating group. In other embodiments $R^4$ is an electron donating group and $R^5$ is a hydrogen. In other embodiments both $R^4$ and $R^5$ are both electron donating groups. In other embodiments both $R^4$ and $R^5$ are hydrogens. In some embodiments, $R^4$ and/or $R^5$ is a saturated or unsaturated, branched or straight chain hydrocarbon moiety. In other embodiments $R^4$ and/or $R^5$ is a saturated or unsaturated, branched or straight chain hydrocarbon moiety covalently linked to one or more aromatic hydrocarbons. In other embodiments, $R^4$ and/or $R^5$ is a saturated or unsaturated, branched or straight chain hydrocarbon moiety covalently linked to a cycloaliphatic group. In other embodiments $R^4$ and/or $R^5$ is a saturated or unsaturated, branched or straight chain hydrocarbon moiety covalently linked to one or more aromatic hydrocarbons and/or one or more cycloaliphatic groups. In yet other embodiments, $R^4$ and/or $R^5$ is one or more cycloaliphatic groups. In yet other embodiments, $R^4$ and/or $R^5$ is one or more aromatic hydrocarbons. In yet other embodiments, $R^4$ and/or $R^5$ is one or more cycloaliphatic groups covalently linked to one or more aromatic hydrocarbons (or vice versa). In yet other embodiments, when $R^1$ is a hydrogen and $R^4$ and $R^5$ are not both a methyl group.

Substituent $R^1$ in Formula I, Formula IA, and/or Formula IB is bonded to a carbon atom at any one of positions 3, 4, 5, or 6. In another embodiment R' is bonded to a carbon atom at any one of positions 4, 5, or 6. In yet another embodiment $R^1$ is bonded to a carbon atom at position 4 or 6. In yet another embodiment $R^1$ is bonded to a carbon atom at position 3. In yet another embodiment $R^1$ is bonded to a carbon atom at position 4. In yet another embodiment $R^1$ is bonded to a carbon atom at position 5. In yet another embodiment $R^1$ is bonded to a carbon atom at position 6. Similarly, $R^2$ is bonded to a carbon atom at any one of positions 9, 10, 11, 12 or 13. In another embodiment $R^2$ is bonded to a carbon atom at any one of positions 10, 11, or 12. In another embodiment $R^2$ is bonded to a carbon atom at any one of positions 9 or 13. In another embodiment $R^2$ is bonded to a carbon atom at any one of positions 10 or 12. In another embodiment $R^2$ is bonded to a carbon atom at position 9. In yet another embodiment $R^2$ is bonded to a carbon atom at position 10. In another embodiment $R^2$ is bonded to a carbon atom at position 11. In another embodiment $R^2$ is bonded to a carbon atom at position 12. In another embodiment $R^2$ is bonded to a carbon atom at position 13.

Substituent $R^1$ in Formula II is bonded to a carbon atom at any one of positions 2, 4, 5, or 6. In another embodiment $R^1$ is bonded to a carbon atom at any one of positions 4, 5, or 6. In yet another embodiment $R^1$ is bonded to a carbon atom at position 4 or 6. In yet another embodiment $R^1$ is bonded to a carbon atom at position 4. In yet another embodiment $R^1$ is bonded to a carbon atom at position 5. In yet another embodiment $R^1$ is bonded to a carbon atom at position 6. Similarly, $R^2$ is bonded to a carbon atom at any one of positions 9, 10, 11, 12 or 13. In another embodiment $R^2$ is bonded to a carbon atom at any one of positions 10, 11, or 12. In another embodiment $R^2$ is bonded to a carbon atom at any one of positions 9 or 13. In another embodiment $R^2$ is bonded to a carbon atom at any one of positions 10 or 12. In another embodiment $R^2$ is bonded to a carbon atom at any one of position 9. In yet another embodiment $R^2$ is bonded to a carbon atom at position 10. In another embodiment $R^2$ is bonded to a carbon atom at position 11. In another embodiment $R^2$ is bonded to a carbon atom at position 12. In another embodiment $R^2$ is bonded to a carbon atom at position 13.

Useful compounds include those of Formula II, wherein one or more selected atoms within one or both of the aryl rings are nitrogen. In particular, antioxidant compounds include compounds wherein there is a nitrogen atom at either position 3 or position 5 of Formula II. Antioxidant compounds also include compounds where there is a nitrogen atom at both positions 3 and 5 of Formula II. Such compounds also include compounds wherein there is a nitrogen atom at positions 3 and 10 of Formula II. Such compounds also include compounds having a nitrogen atom at positions 3 and 12 of Formula II. In another embodiment, such compounds include compounds wherein there is a nitrogen atom at positions 3, 5, and 10 of Formula II. In another embodiment, antioxidant compounds include compounds wherein there is a nitrogen atom at positions 3, 5, and 12 of Formula II. In another embodiment, antioxidant compounds include compounds wherein there is a nitrogen atom at positions 3, 5, 10 and 12 of Formula II. In another embodiment, compounds are those wherein X, Y, and Z are each nitrogen. In another embodiment, compounds are those wherein X is nitrogen, and Y and Z are carbon. In another embodiment, compounds are those wherein X and Y are nitrogen and Z is carbon. In another embodiment, compounds are those wherein Y is nitrogen, and X and Z are carbon. In another embodiment, compounds are those wherein Y and Z are nitrogen, and X is carbon.

Antioxidant compounds also encompass those of Formula II wherein $R^1$ and $R^2$ are each independently: (i) a hydrogen; (ii) a $C_2$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_2$ to $C_{20}$ hydrocarbon group; and wherein $R^1$ and $R^2$ are not both hydrogen. Antioxidant compounds also encompass those of Formula II wherein $R^1$ and $R^2$ are each independently: (i) a hydrogen; (ii) a $C_1$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In another embodiment, compounds are those of Formula II wherein $R^1$ is attached to a carbon at position 2 or 6, and is: a hydrogen; (ii) a $C_1$ to $C_3$ hydrocarbon group; (iii) $OR^3$ wherein $R^3$ is a hydrogen or a $C_1$ to $C_3$ hydrocarbon group; or (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In another embodiment, compounds are those of Formula II wherein $R^2$ is attached to a carbon at position 9 or 13, and is: (i) a hydrogen; (ii) a $C_1$ to $C_3$ hydrocarbon group; (iii) $OR^3$ wherein $R^3$ is a hydrogen or a $C_1$ to $C_3$ hydrocarbon group; or (iv) $NR^4R^5$ wherein $R^4$ and $R^5$ are each independently hydrogen or a $C_1$ to $C_3$ hydrocarbon group; and wherein $R^1$ and $R^2$ are not both hydrogen.

In another embodiment, compounds are those of Formula II wherein $R^1$ is attached to a carbon at position 5, and is: (i) a hydrogen; (ii) a $C_1$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In another embodiment, compounds are those of Formula II wherein $R^2$ is attached to a carbon at position 10 or 12, and is: (i) a hydrogen;
(ii) a $C_1$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In another embodiment, compounds are those of Formula II wherein $R^1$ is attached to a carbon at position 4, and is: (i) a hydrogen; (ii) a $C_1$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In another embodiment, compounds are those of Formula II wherein $R^2$ is attached to a carbon at position 11, and is: (i) a hydrogen; (ii) a $C_1$ to $C_{20}$ hydrocarbon group; (iii) $OR^3$ wherein $R^3$ is a hydrogen or a $C_1$ to $C_{20}$ hydrocarbon group; or (iv) $NR^4R^5$ wherein $R^4$ and $R^5$ are each independently hydrogen or a $C_1$ to $C_{20}$ hydrocarbon group; and wherein $R^1$ and $R^2$ are not both hydrogen.

In some embodiments, $R^4$ and $R^5$ are not both hydrogen. In some embodiments $R^3$ is not hydrogen. In some embodiments none of $R^3$, $R^4$, or $R^5$ are hydrogen.

solubility in aqueous environment to test their efficacy in acidic (pH=4) and neutral environment (pH=7).

To evaluate the effect of an added sacrificial base on the high-temperature radical-trapping activity of antioxidants, autoxidations of n-hexadecane were carried out at 160° C. in a stirred flow reactor in the absence of or presence of a base, where a constant positive pressure of $O_2$ was used to stir the medium and prevent mass transfer from becoming rate limiting (Igarashi, J., et al., *J. Am. Chem. Soc.* 1992, 114, 7727; Jensen, R.; et al., *J. Am. Chem. Soc.* 1979, 101, 7574). Tetralin hydroperoxide (10 mM) was used as a radical initiator since inhibited autoxidations in the absence of an initiator were very slow. At regular intervals, aliquots of the reaction mixture were removed, cooled and the concentration of hydroperoxide products determined by reaction with a developed fluorogenic phosphine (Hanthorn, J. J., et al., *Chem. Commun.* 2012, 48, 10141). Autoxidations were followed for the first 2% of the reaction, based on hydroperoxide formation, since beyond ca. 3% conversion, the hydroperoxide yield begins to decrease and highly complex mixtures of ketones, alcohols, carboxylic acids and esters arise. Results are shown in the figures.

Hydrocarbon autoxidation produces carboxylic acids from the very early stages of the reaction in addition to hydroperoxides. Korcek and co-workers suggested that they arise primarily from fragmentation of γ-hydroperoxyketones by a concerted mechanism. When acid formation was monitored over an initial period (first 2400 s) of an autoxidation of n-hexadecane directly by electrospray ionization mass spectrometry, it was found that the total acid concentration was already roughly 25% of the hydroperoxide concentration (~15 mM vs. ~60 mM).

Scheme 1. Proposed mechanism of acid formation in the early stages of hydrocarbon autoxidations.

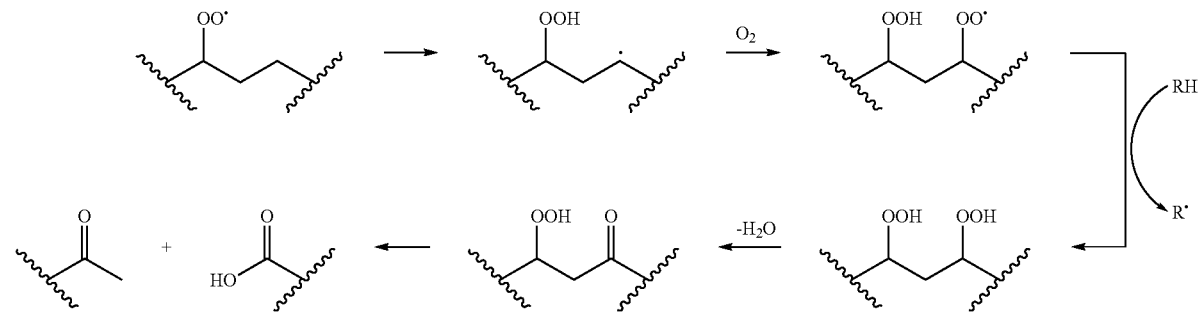

Figure 2B:
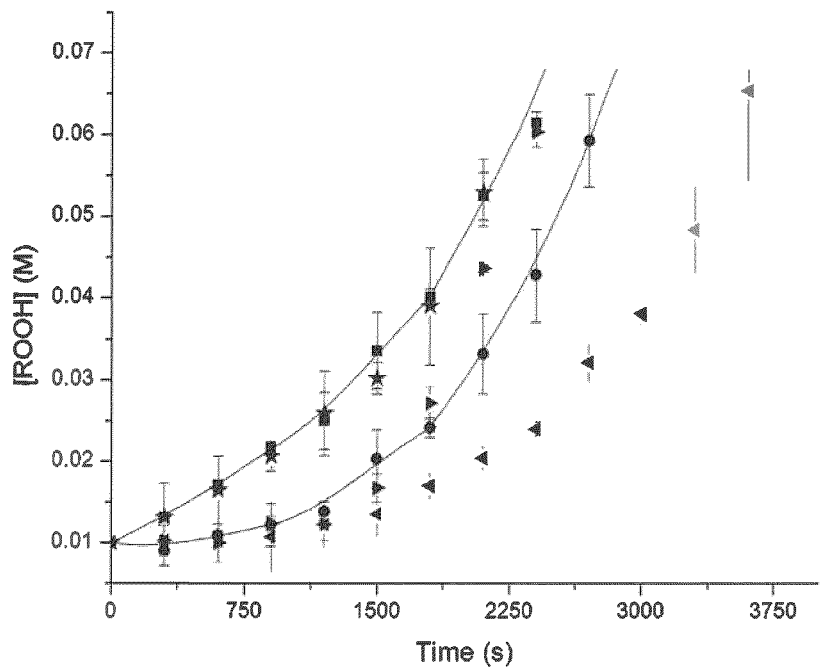
FIG. 2B shows data pertaining to hydroperoxide formation in the autoxidation of hexadecane at 160° C. initiated by 10 mM tetralin hydroperoxide (■) in the presence of 40 μM of 4 (◄), 5 (►) 6 (★) or 7 (●).
Figure 7:
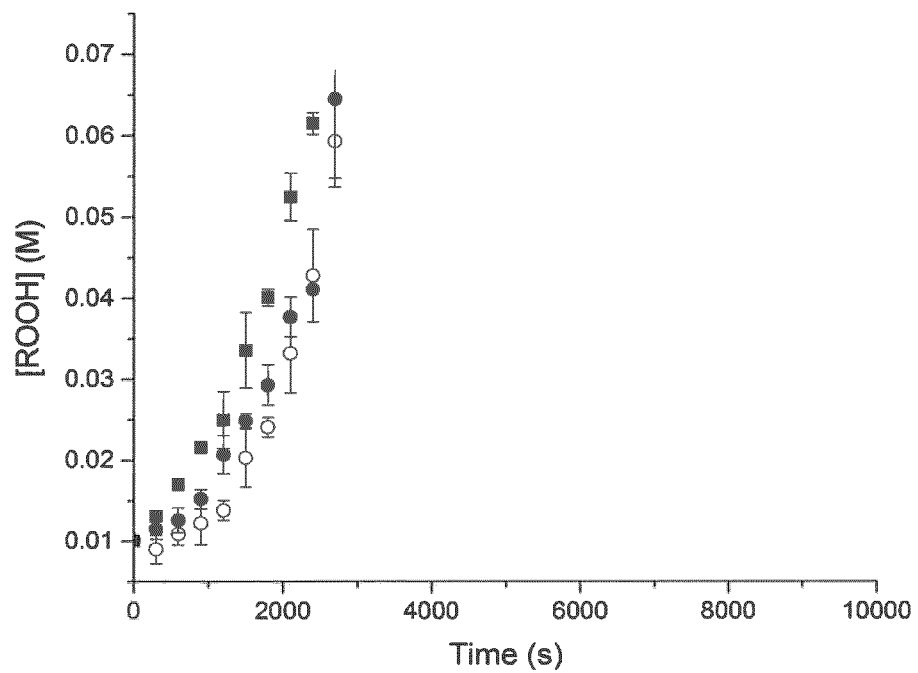
FIG. 7 graphically displays oxidation product (hydroperoxide) formation in an autoxidation of n-hexadecane at 160° C. initiated by 10 mM tetralin hydroperoxide: in the absence of antioxidant and the absence of a base (■); in the presence of antioxidant compound 7 (40 µM) and the absence of a base (○); and in the presence of antioxidant compound 7 (40 µM) and in the presence of a base, specifically 2,4,6-tri-tert-butylpyridine (1 mM) (●).
Figure 8:
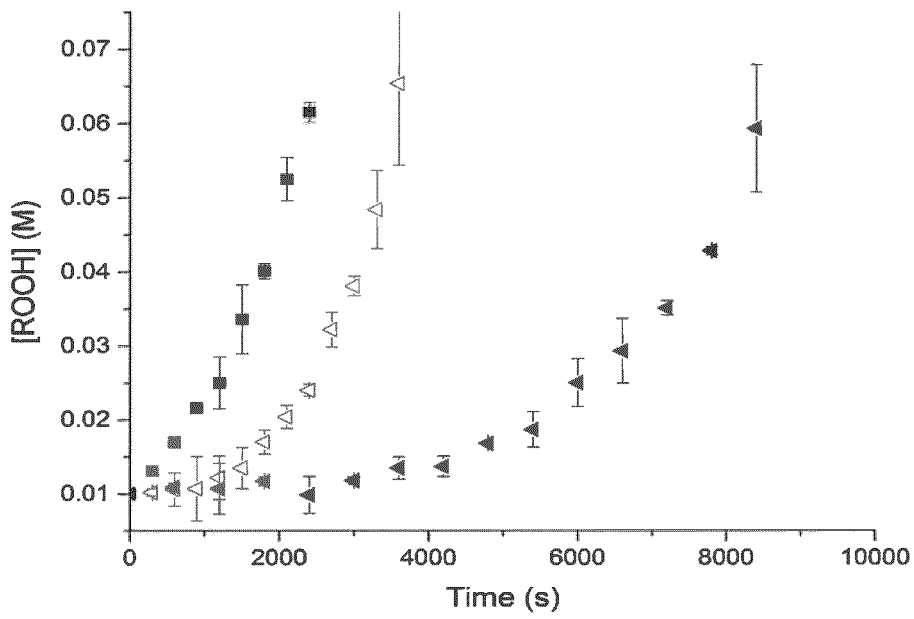
FIG. 8 graphically displays oxidation product (hydroperoxide) formation in an autoxidation of n-hexadecane at 160° C. initiated by 10 mM tetralin hydroperoxide: in the absence of antioxidant and the absence of a base (■); in the presence of antioxidant compound 4 (40 µM) and the absence of a base (◁); and in the presence of antioxidant compound 4 (40 µM) and in the presence of a base, specifically 2,4,6-tri-tert-butylpyridine (1 mM) (◄).

Compounds whose structural formulae are shown in FIG. 1 were selected for study based on their reactivity toward peroxyl radicals (high $k_1$, i.e. 1-3, 24, 26), stability toward oxidation (high $E^0$, i.e. 6), or balance of these two characteristics (i.e. 4-5, 22). Compounds 20 and 23 were employed in order to prevent the addition of peroxyl radical to the para-position of the aromatic ring. Compound 25 was used similarly in order to increase the stability of Compound 3 towards peroxyl radical addition. These compounds are substituted with longer alkyl chains in order to ensure their solubility in heavy hydrocarbons and low volatility at elevated temperatures (see Working Examples for synthetic preparation). Diarylamine 7 is representative of industry standard alkylated diphenylamines. Compounds 21-26 are substituted with shorter alkyl chain to ensure their complete To assess whether acid suppresses the reactivity of the heterocyclic diarylamines, palmitic acid, a non-volatile saturated carboxylic acid, was added to an autoxidation inhibited by representative compound 4. In the event, as little as 1 mM acid was found to disrupt the inhibitory activity of 4, but that of the less basic diphenylamine 7 (a standard) was unchanged, as was the course of the uninhibited oxidation. In light of these results, a base was added to an autoxidation inhibited by 4 in an attempt to 'rescue' its radical-trapping antioxidant activity. In the presence of the non-volatile, non-nucleophilic base 2,4,6-tri-tert-butylpyridine (TTBP, 1 mM), an unprecedented inhibited period was observed (see FIGS. 2H and 8). Importantly, the addition of base had no effect on the activity of diphenylamine 7 (see FIGS. 2H and 7)(or the uninhibited rate of oxidation), suggesting that the acid produced early in the autoxidation was sufficient to deactivate the heterocyclic diarylamine 4, but not diphenylamine 7. The activity of 4 was also rescued by cesium carbonate, potassium carbonate, or a tert-alkylated primary amine (Primene™ 81-R), underscoring that its inactivation is due to protonation. Although TTBP, cesium carbonate, potassium carbonate and Primene™ 81-R have been used in the studies described herein, other sacrificial bases would also be effective. Common metals that can be used to make neutral or basic additives include sodium, potassium, magnesium, calcium, and barium. Calcium and magnesium find most extensive use as lubricant additives, with a preference for calcium due to its lower cost. Accordingly, bases can include metal oxides, hydroxides, and carbonates.

Figure 9:
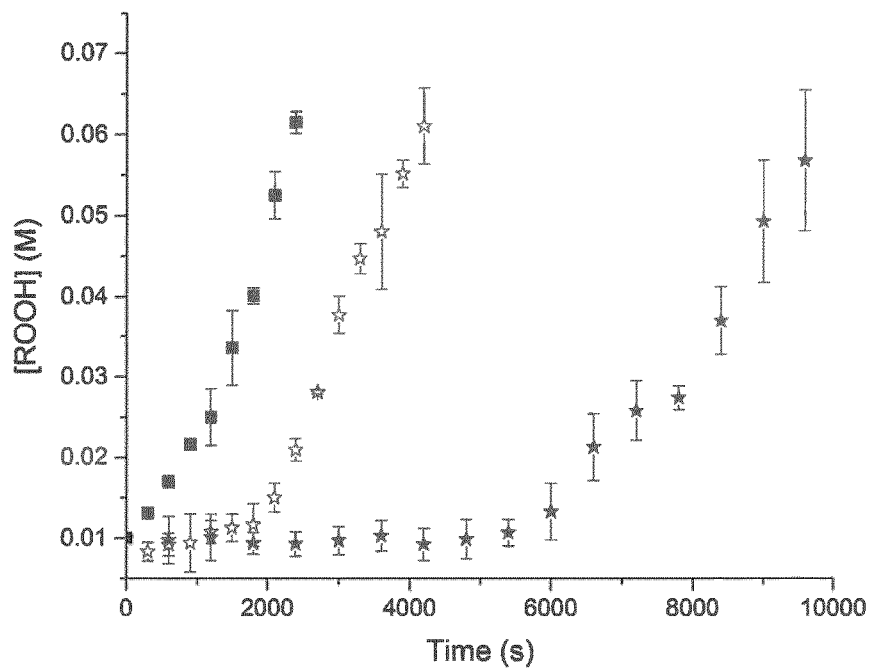
FIG. 9 graphically displays oxidation product (hydroperoxide) formation in an autoxidation of n-hexadecane at 160° C. initiated by 10 mM tetralin hydroperoxide: in the absence of antioxidant and the absence of a base (■); in the presence of antioxidant compound 20 (40 µM) and the absence of a base (☆); and in the presence of antioxidant compound 20 (40 µM) and in the presence of a base, specifically 2,4,6-tri-tert-butylpyridine (1 mM) (★).
Figure 10:
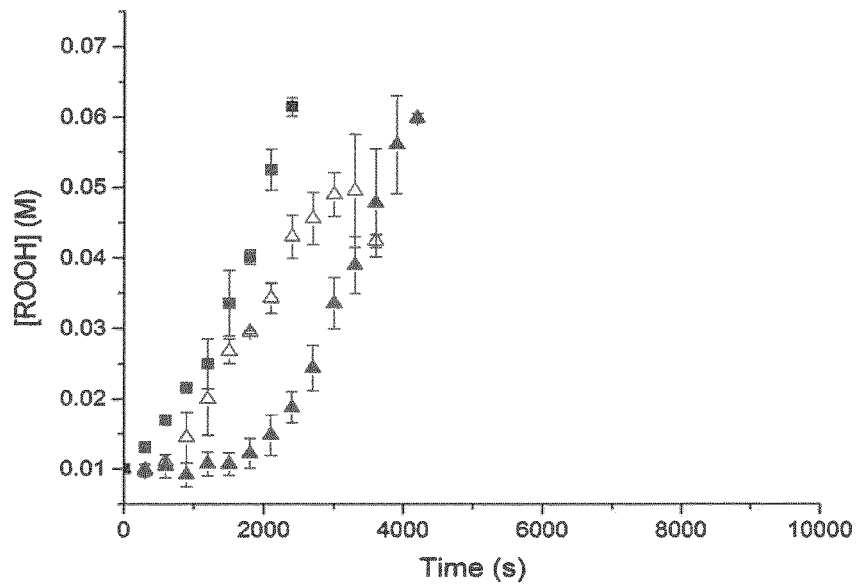
FIG. 10 graphically displays oxidation product (hydroperoxide) formation in an autoxidation of n-hexadecane at 160° C. initiated by tetralin hydroperoxide (10 mM): in the absence of antioxidant and the absence of a base (■); in the presence of antioxidant compound 3 (40 µM) and the absence of a base (Δ); and in the presence of antioxidant compound 3 (40 µM) and in the presence of a base, specifically 2,4,6-tri-tert-butylpyridine (1 mM) (▲).
Figure 11:
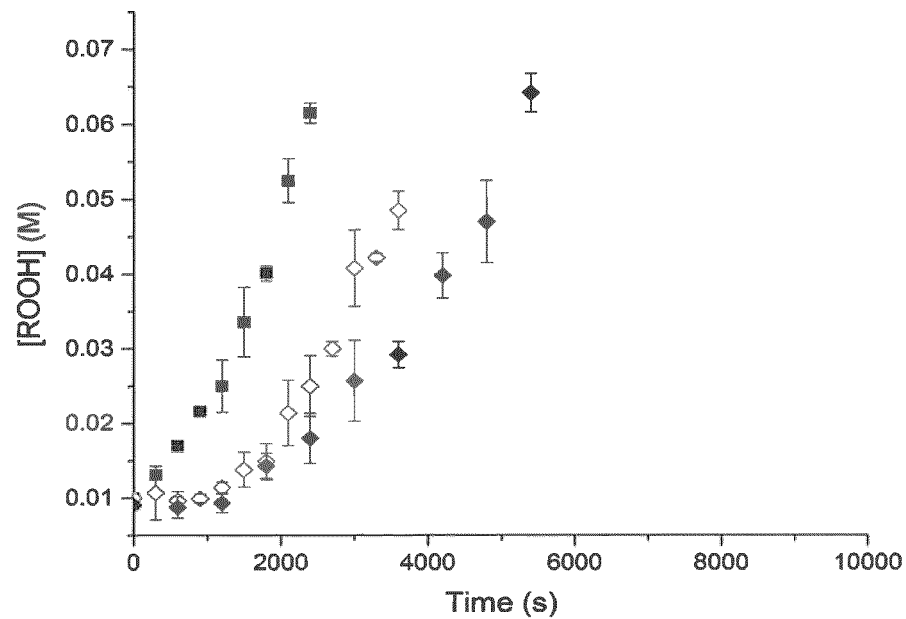
FIG. 11 graphically displays oxidation product (hydroperoxide) formation in an autoxidation of n-hexadecane at 160° C. initiated by tetralin hydroperoxide (10 mM): in the absence of antioxidant and the absence of a base (■); in the presence of antioxidant compound 2 (40 µM) and the absence of a base (◇); and in the presence of antioxidant compound 2 (40 µM) and in the presence of a base, specifically 2,4,6-tri-tert-butylpyridine (1 mM) (♦).
Figure 12:
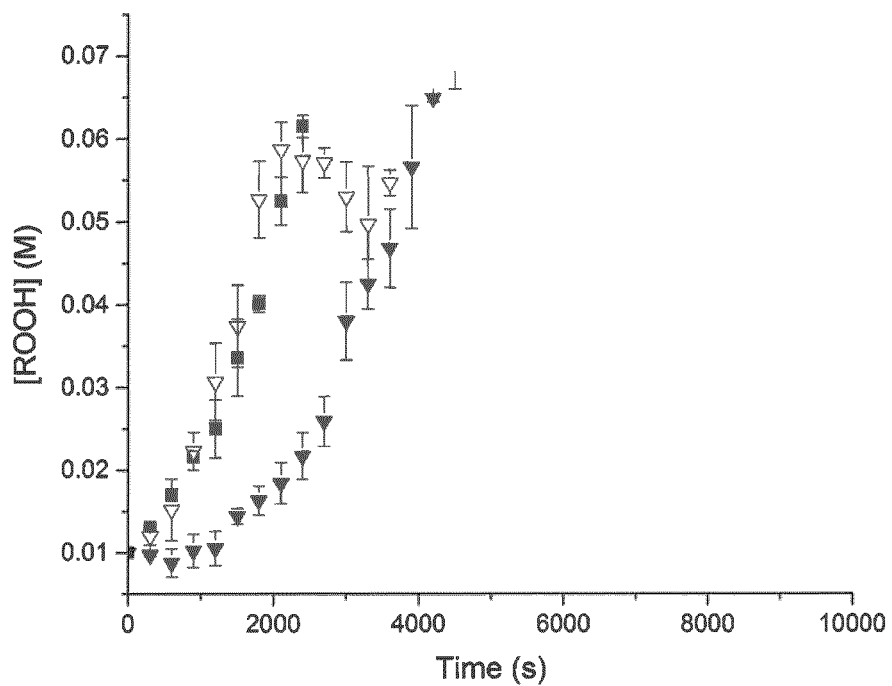
FIG. 12 graphically displays oxidation product (hydroperoxide) formation in an autoxidation of n-hexadecane at 160° C. initiated by tetralin hydroperoxide (10 mM): in the absence of antioxidant and the absence of a base (■); in the presence of antioxidant compound 1 (40 µM) and the absence of a base (∇); and in the presence of antioxidant compound 1 (40 µM) and in the presence of a base, specifically 2,4,6-tri-tert-butylpyridine (1 mM) (▼).
Figure 13:
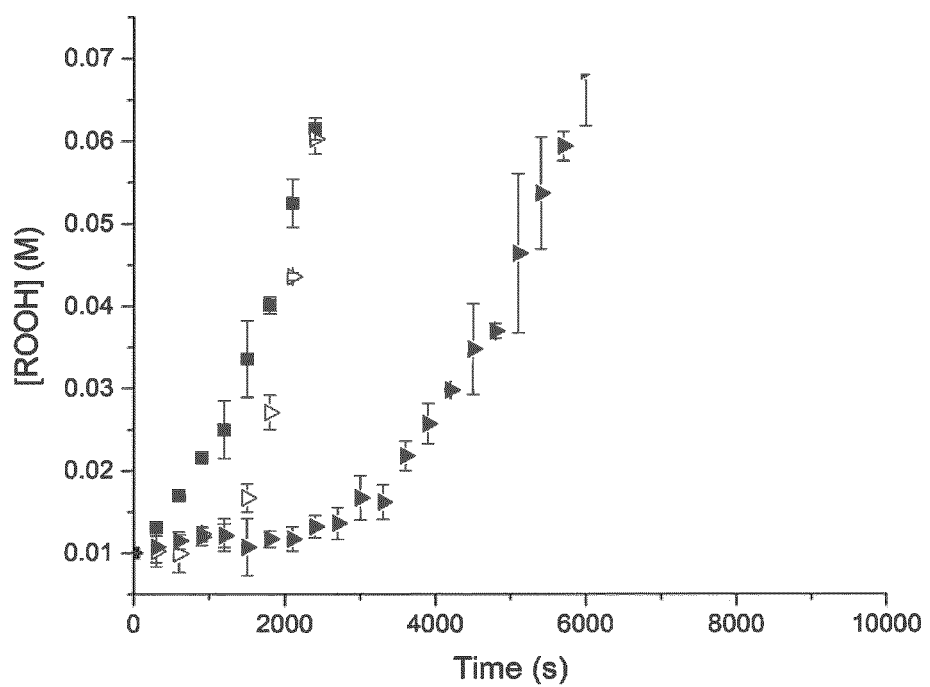
FIG. 13 graphically displays oxidation product (hydroperoxide) formation in an autoxidation of n-hexadecane at 160° C. initiated by tetralin hydroperoxide (10 mM): in the absence of antioxidant and the absence of a base (■); in the presence of antioxidant compound 5 (40 µM) and the absence of a base (▷); and in the presence of antioxidant compound 5 (40 µM) and in the presence of a base, specifically 2,4,6-tri-tert-butylpyridine (1 mM) (►).
Figure 14:
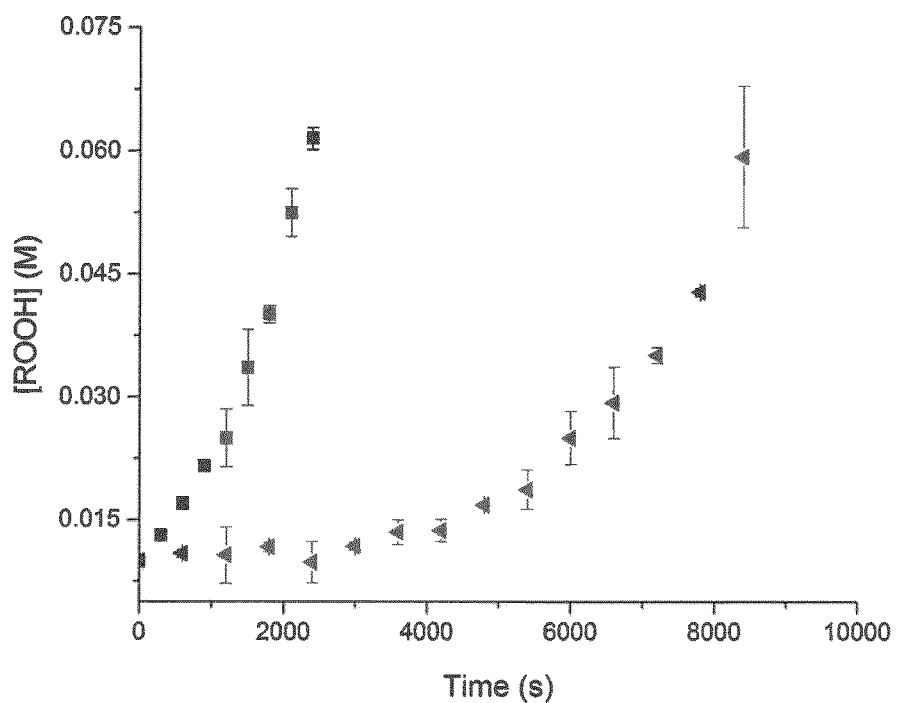
FIG. 14: graphically displays oxidation product (hydroperoxide) formation in an autoxidation of n-hexadecane at 160° C. initiated by tetralin hydroperoxide (10 mM): in the absence of an antioxidant (■); and in the presence of antioxidant 4 (40 µM) and in the presence of a base, specifically, 2,4,6-tri-tert-butylpyridine (1 mM) (◄).
Figure 15:
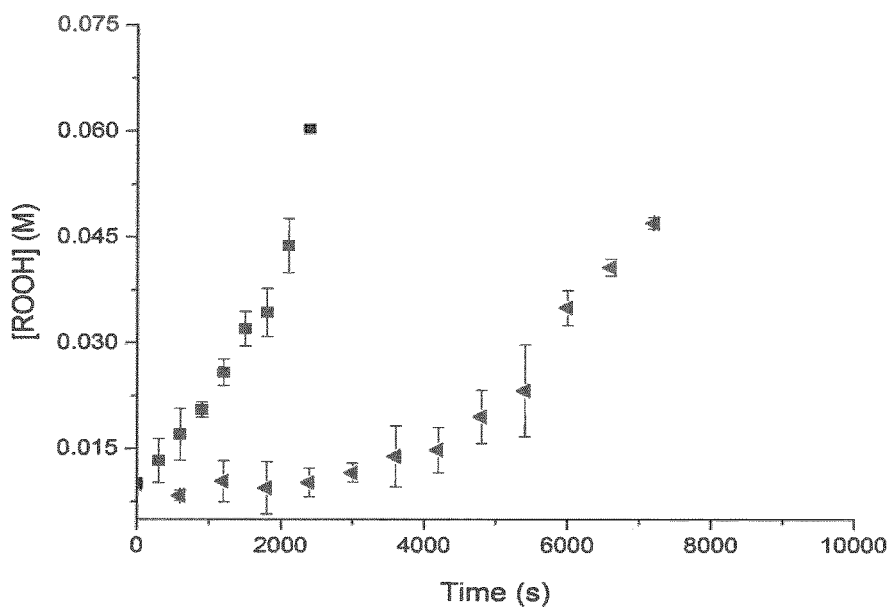
FIG. 15: graphically displays oxidation product (hydroperoxide) formation in an autoxidation of n-hexadecane at 160° C. initiated by tetralin hydroperoxide (10 mM): in the absence of an antioxidant (■); and in the presence of antioxidant 4 (40 µM) and in the presence of a base, specifically, Primene-81R (1 mM) (◄).
Figure 16:
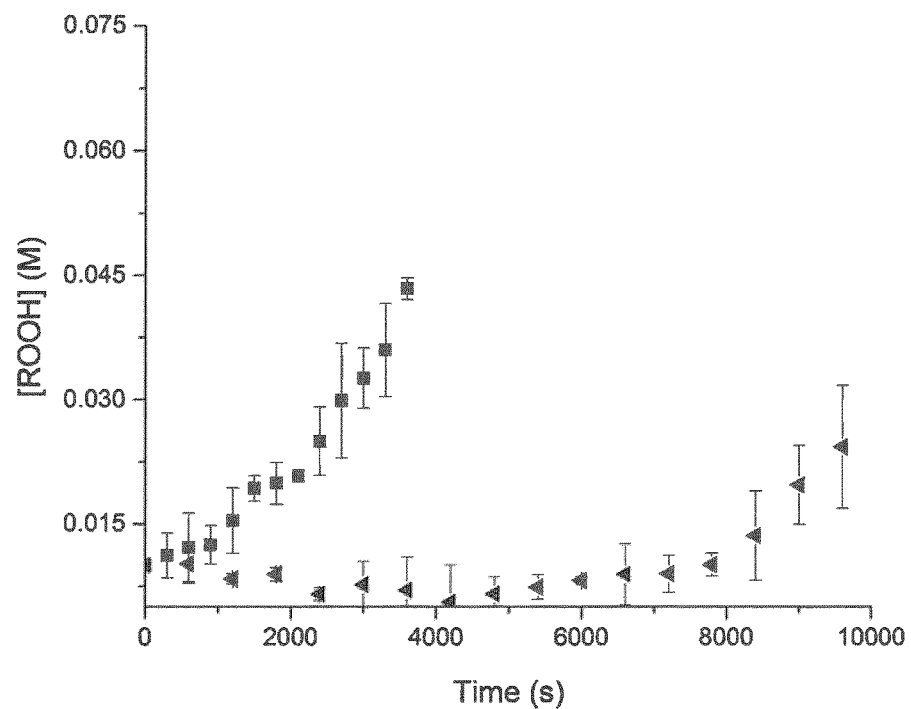
FIG. 16 graphically displays oxidation product (hydroperoxide) formation in an autoxidation of n-hexadecane at 160° C. initiated by tetralin hydroperoxide (10 mM): in the absence of an antioxidant (■); and in the presence of antioxidant 4 (40 μM) and in the presence of a base, specifically, cesium carbonate (1 mM) (◄).
Figure 17:
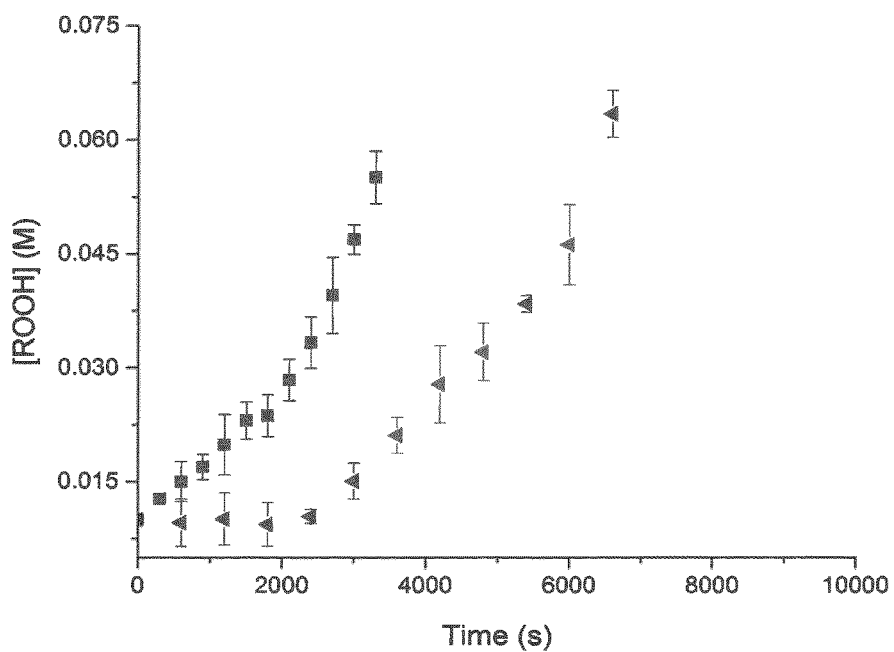
FIG. 17 graphically displays oxidation product (hydroperoxide) formation in an autoxidation of n-hexadecane at 160° C. initiated by tetralin hydroperoxide (10 mM): in the absence of an antioxidant (■); and in the presence of antioxidant 4 (40 μM) and in the presence of a base, specifically, potassium carbonate (1 mM) (◄).

Consistent with the foregoing, the $pK_a$ of the conjugate acid of 4 was determined to be almost 4 units greater than the conjugate acid of 7 (8.2±0.2 vs. 4.6±0.3 in 4:1 $CH_3CN$:$H_2O$). In fact, each of the reactive heterocyclic diarylamines (1-5) were found to be significantly more basic than the diphenylamine, with $pK_a$s of the corresponding conjugate acids of 9.8±0.1 (1), 8.8±0.1 (2), 8.4±0.1 (3) and 8.3±0.1 (5). Accordingly, autoxidations were much better inhibited by these compounds in the presence of added base (see FIG. 2I). Interestingly, even the pyridine-containing compounds 1 and 3, which were found to be relatively unstable to 02 at 160° C., were superior to 7. This is presumably because the balance of either 1 or 3 that remain over the course of the autoxidation are highly potent. The pyrimidine-containing compounds 2, 4, and 5 were particularly good, presumably due to a compromise between stability and reactivity. Efforts to increase the stability of compound 4 by designing and making compound 20, which has a tert-butyl group in the para-position led to slightly increased stability and reactivity (see FIG. 9).

The unprecedented inhibited periods observed for the heterocyclic diarylamines in the presence of base must result from increased stoichiometry for the reactions of these amines with peroxyl radicals, arising from one (or both) of: faster/more efficient regeneration of the diarylamine from its corresponding alkoxyamine, and/or fewer deleterious off-cycle reactions (recall the catalytic cycle in Chart 2). The mechanism of diphenylamine regeneration was studied, and results revealed that either a retro-carbonyl-ene reaction or N—O dissociation/disproportionation pathway operates depending on the structure of the diarylamine and/or substrate. Those studies were enabled by the synthesis of authentic alkoxyamines derived from diphenylamine and 4,4'-di-tert-butyldiphenylamine. Unfortunately, attempts to prepare authentic alkoxyamines derived from 1-5 have not been successful, precluding determination of the kinetics of diarylamine regeneration for these compared to 7. However, CBS-QB3 computations of the N—O BDEs in model (O—$CH_3$) alkoxyamines derived from 4 and 7 suggest that regeneration of diarylamine 4 requires 2.3 kcal/mol less energy than regeneration of 7, which corresponds to a 14-fold increase in rate at 160° C.—in good agreement with the observed 12.5-fold difference in $\Delta t_{2\%}$ (moreover, in the presence of 4, the maximum oxidation rate has still not been reached at 2% conversion, see FIG. 2I).

Although it has been demonstrated that carboxylic acids that are produced in the autoxidation of hydrocarbons can mask the greater efficacy of the heterocyclic diarylamines, this can be unmasked by addition of base to the autoxidizing hydrocarbon. Of the wide variety of applications wherein the compounds described above may have a significant impact, the most tangible would be increasing maintenance intervals on automobile and jet engines, and enabling the development of more efficient combustion engines, which necessarily run at higher temperatures and require lubricants containing more effective radical-trapping antioxidants.

In certain embodiments, one or more antioxidant compounds may be combined with a base and one or more organic substrates to form compositions wherein the antioxidant assists in protecting the organic substrate from oxidative degradation, and the base prevents degradation of the antioxidant or reduces the level of degradation of the antioxidant.

Therefore, a base and one or more antioxidants are combined with one or more organic substrates to form compositions wherein the compounds are added in an effective amount to ensure sufficient antioxidant activity to reduce or inhibit the level of degradation of the organic substrate(s) within the composition when compared with the level of degradation that occurs to the organic substrate in the absence of base and an antioxidant. As described herein, the presence of a sacrificial base has been shown to significantly augment performance of certain antioxidants.

A base and one or more antioxidant compounds may also be combined with one or more organic substrates to scavenge free radicals in a composition containing the organic substrate(s).

A base and one or more antioxidant compounds may also be combined with compounds required for the synthesis of an organic substrate such as a polymer. The compounds required for the synthesis can include organic substrates themselves, for example monomers which will react to form a polymer. The one or more antioxidant compounds are useful in scavenging at least one free radical species which may exist or be formed by the monomers, and therefore may improve the yield, stability and/or longevity of the organic substrate and/or the monomers which form the polymer.

A base and one or more antioxidant compounds are added, blended, sprayed, adhered, used to cover, impregnate or are otherwise combined with one or more organic substrates to form compositions of the invention.

In some embodiments, a base and antioxidant compound(s) are added to organic substrates which are natural or synthetic polymers such as alpha-olefin polymers, polyamides, polyesters, polyacetals, acrylonitrile-butadiene-styrene thermoplastics, and other resin or rubber polymers to protect the polymers against excessive breakdown during the synthesis, aging, and/or heat treatment involved in the making or use. For example, a base and antioxidant compound(s) can be added during the synthesis of one or more polymers and preferentially react with, and/or decompose free radicals that are generated during the synthesis of a polymer to thereby prevent or reduce activities which prevent effective polymerization and/or degradation during the preparation of the polymer. Addition of antioxidants to one or more polymers during the preparation and/or use is well known in the art. See for example U.S. Pat. No. 2,543,329 which describes the stabilization of polyethylene with diphenylamine; U.S. Pat. No. 3,072,603 describes the stabilization of poly-alpha-olefins by use of a stabilizer combination consisting of a diester of 3,3'-thiodipropionic acid and para substituted diphenylamines which contain alkyl group substitutions of $C_1$ to $C_{12}$ in length. Both U.S. Pat. Nos. 2,543,329 and 3,072,603, without adopting any definitions as found therein, are incorporated herein by reference.

In other embodiments, a base and antioxidant compound(s) are added to organic substrates which are typically used in the cosmetic and/or pharmaceutical industry including those oils, fats and/or waxes comprised of esters of saturated and/or monounsaturated and/or polyunsaturated fatty acids, including the unsaponifiable fractions obtained from such oils, fats and waxes so as to scavenge free radicals that may exist or be formed in the preparation or use of the cosmetic and/or pharmaceutical product. See for example U.S. Pat. No. 5,672,574 as well as a description of the type of lipids used for this applications as described in Rabasco Alvarez, A. M., and Gonzalez Rodriguez, M. L. "Lipids in pharmaceutical and cosmetic preparations" Grases y Aceites Vol. 51, Fasc. 1-2 (2000) 74-96.

Figure 18:
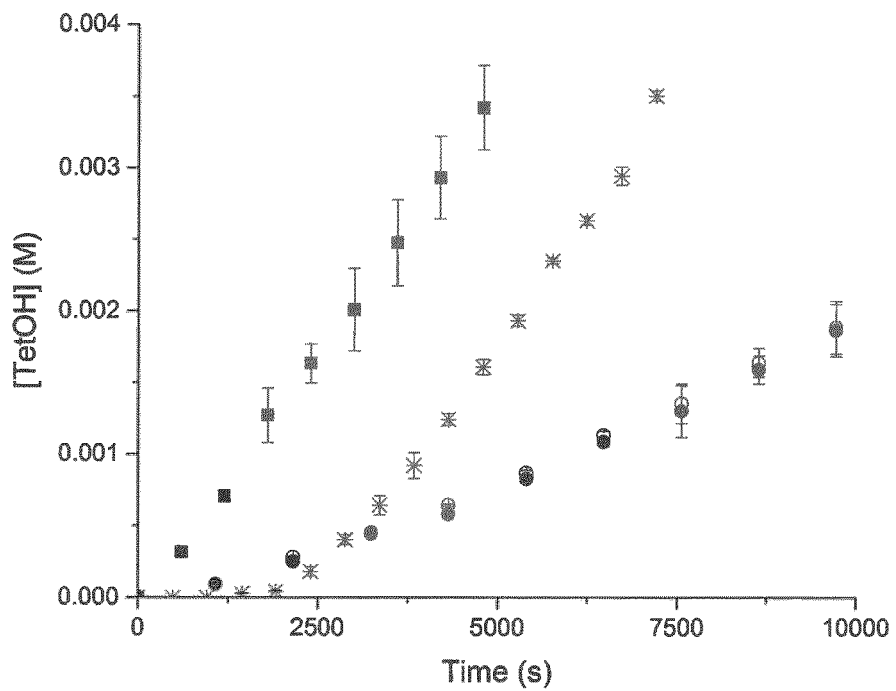
FIG. 18 graphically displays oxidation product (hydroperoxide) formation in an autoxidation of tetralin at 70° C. initiated by azobis(α-tetralin) (0.1 mM): in the absence of antioxidant and the absence of an acid (■); in the presence of antioxidant 7 (2 μM) and in the absence of an acid (○); and in the presence of antioxidant 7 (2 μM) and in the presence of an acid, specifically of hexanoic acid (50 μM) (●). A plot of 2,2,5,7,8-pentamethyl-6-chromanol (a derivative of Vitamin E, 2 μM) (*) is shown for comparison.
Figure 19:
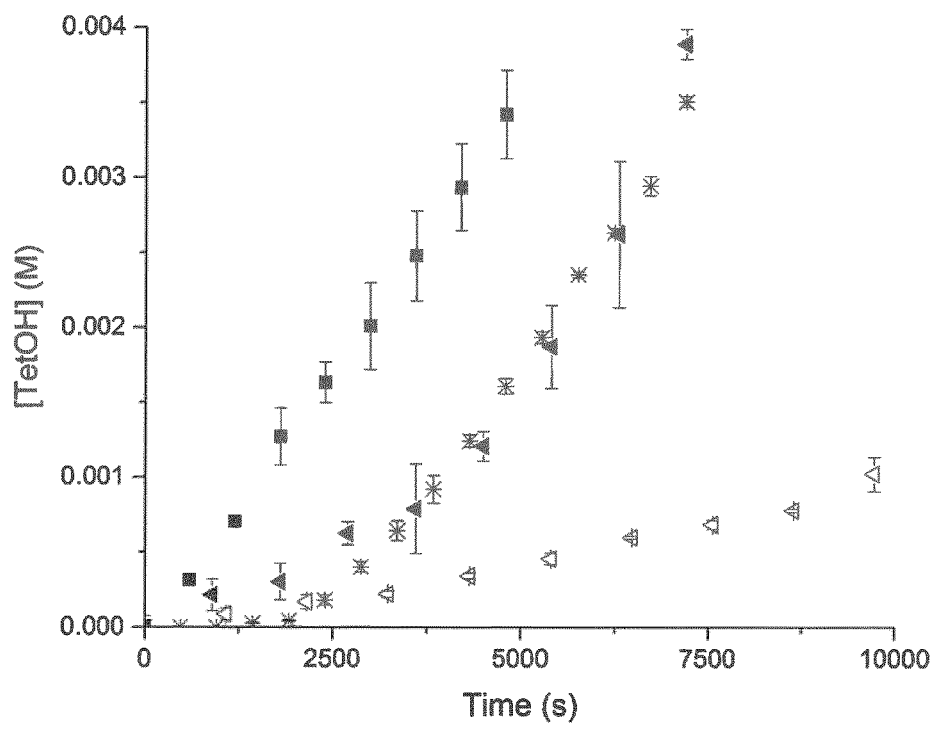
FIG. 19 graphically displays oxidation product (hydroperoxide) formation in an autoxidation of tetralin at 70° C. initiated by azobis(α-tetralin) (0.1 mM): in the absence of antioxidant and the absence of an acid (■); in the presence of antioxidant 4 (2 μM) and in the absence of an acid (◁) and in the presence of antioxidant 4 (2 μM) and in the presence of an acid, specifically of hexanoic acid (50 μM) (◄). A plot of 2,2,5,7,8-pentamethyl-6-chromanol (a derivative of Vitamin E, 2 μM) (*) is shown for comparison.
Figure 20A:
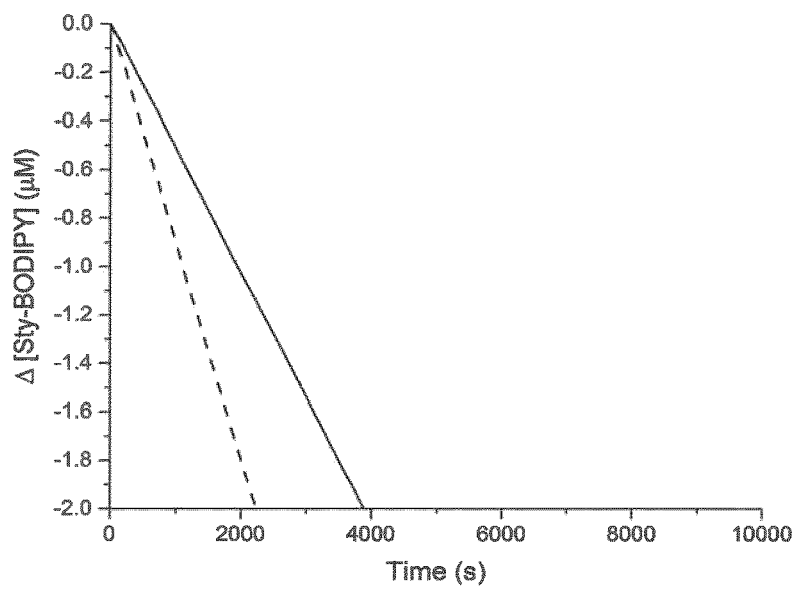
FIG. 20A Co-oxidations of 25% THF in aqueous buffer of pH 4 and fluorescent dye Sty-BODIPY (10 μM), initiated with AAPH (833 μM) at 37° C.: in the absence of an antioxidant (dashed line); and in the presence of an antioxidant, specifically, compound 21 (2 μM) (solid line). Reaction progress was monitored by absorbance at 562 nm ($\varepsilon$=132,261 $M^{-1}$ $cm^{-1}$).
Figure 20B:
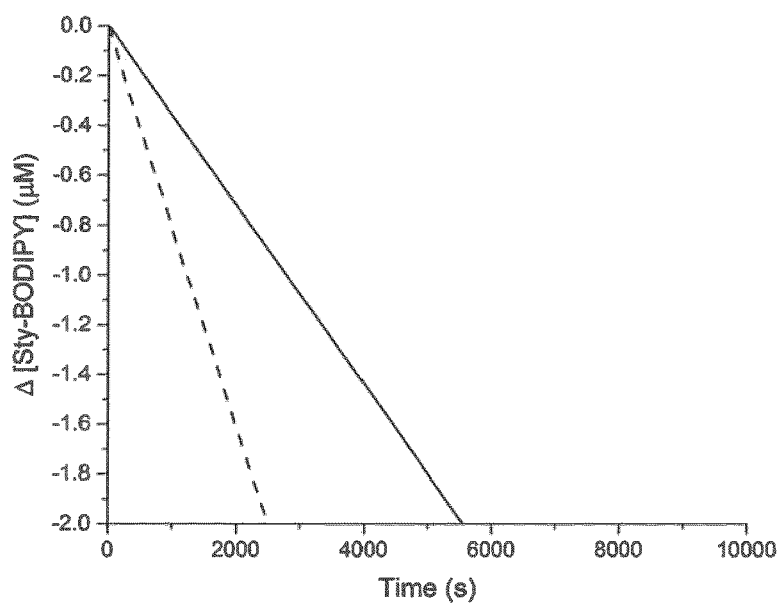
FIG. 20B Co-oxidations of 25% THF in aqueous buffer of pH 10 and Sty-BODIPY (10 μM), initiated with MPH (833 μM) at 37° C.: in the absence of an antioxidant (dashed line); and in the presence of an antioxidant, specifically, compound 21 (2 μM) (solid line). Reaction progress was monitored by absorbance at 562 nm ($\varepsilon$=132,261 $M^{-1}$ $cm^{-1}$).
Figure 21A:
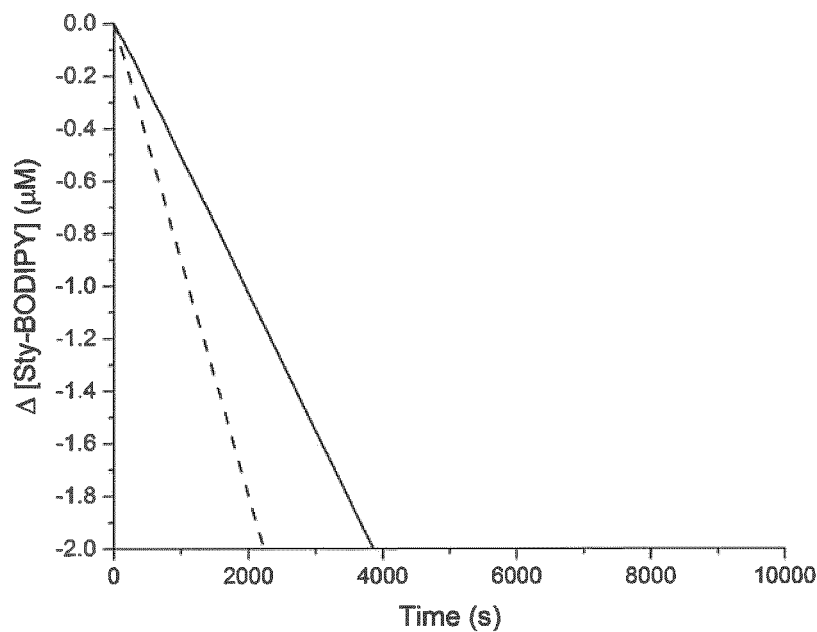
FIG. 21A Co-oxidations of 25% THF in aqueous buffer of pH 4 and Sty-BODIPY (10 μM), initiated with AAPH (833 μM) at 37° C.: in the absence of an antioxidant (dashed line); and in the presence of an antioxidant, specifically, compound 22 (2 μM) (solid line). Reaction progress was monitored by absorbance at 562 nm ($\varepsilon$=132,261 $M^{-1}$ $cm^{-1}$).
Figure 21B:
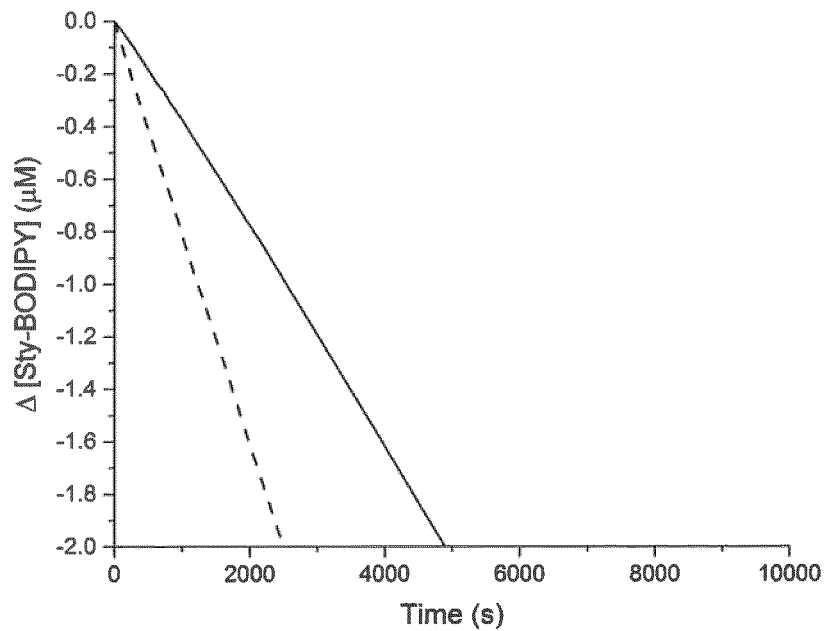
FIG. 21B Co-oxidations of 25% THF in aqueous buffer of pH 10 and Sty-BODIPY (10 μM), initiated with MPH (833 μM) at 37° C.: in the absence of an antioxidant (dashed line); and in the presence of an antioxidant, specifically, compound 22 (2 μM) (solid line). Reaction progress was monitored by absorbance at 562 nm ($\varepsilon$=132,261 $M^{-1}$ $cm^{-1}$).
Figure 22A:
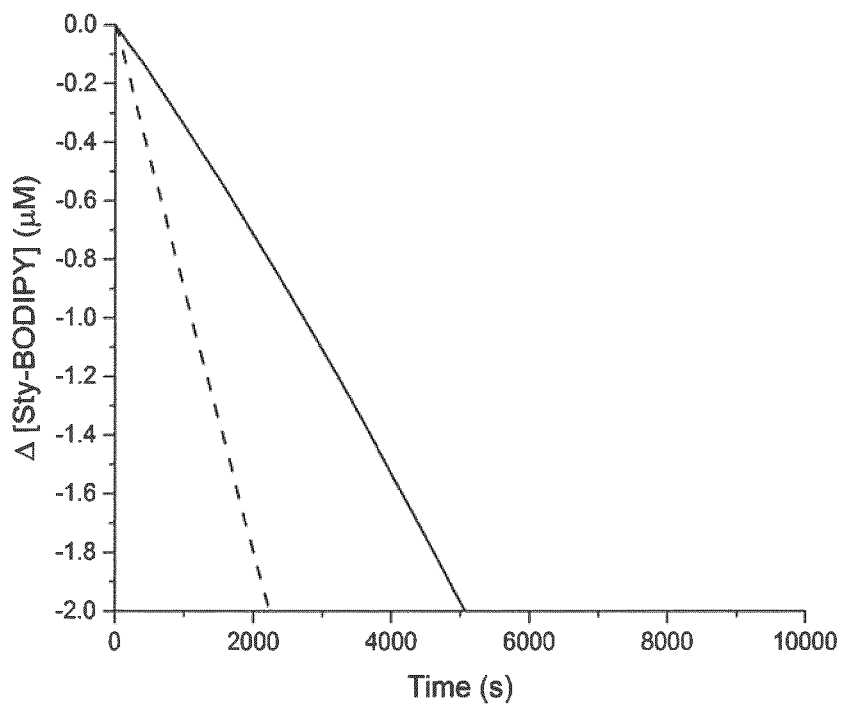
FIG. 22A Co-oxidations of 25% THF in aqueous buffer of pH 4 and Sty-BODIPY (10 μM), initiated with AAPH (833 μM) at 37° C.: in the absence of an antioxidant (dashed line); and in the presence of an antioxidant, specifically, compound 2 μM of 23 (solid line). Reaction progress was monitored by absorbance at 562 nm ($\varepsilon$=132,261 $M^{-1}$ $cm^{-1}$).
Figure 22B:
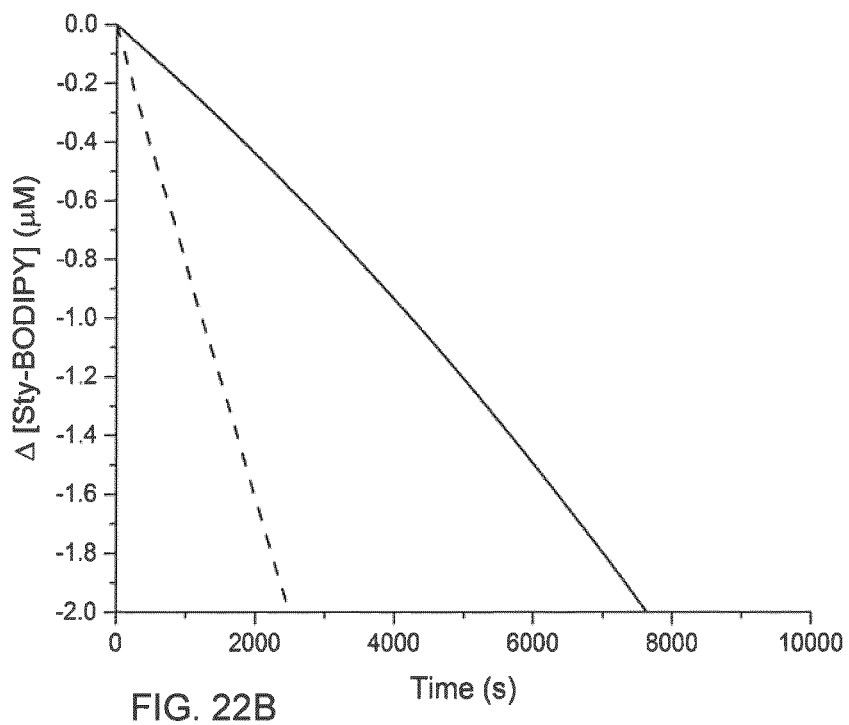
FIG. 22B Co-oxidations of 25% THF in aqueous buffer of pH 10 and Sty-BODIPY (10 μM), initiated with MPH (833 μM) at 37° C.: in the absence of an antioxidant (dashed line); and in the presence of an antioxidant, specifically, compound 2 μM of 23 (solid line). Reaction progress was monitored by absorbance at 562 nm ($\varepsilon$=132,261 $M^{-1}$ $cm^{-1}$).
Figure 23A:
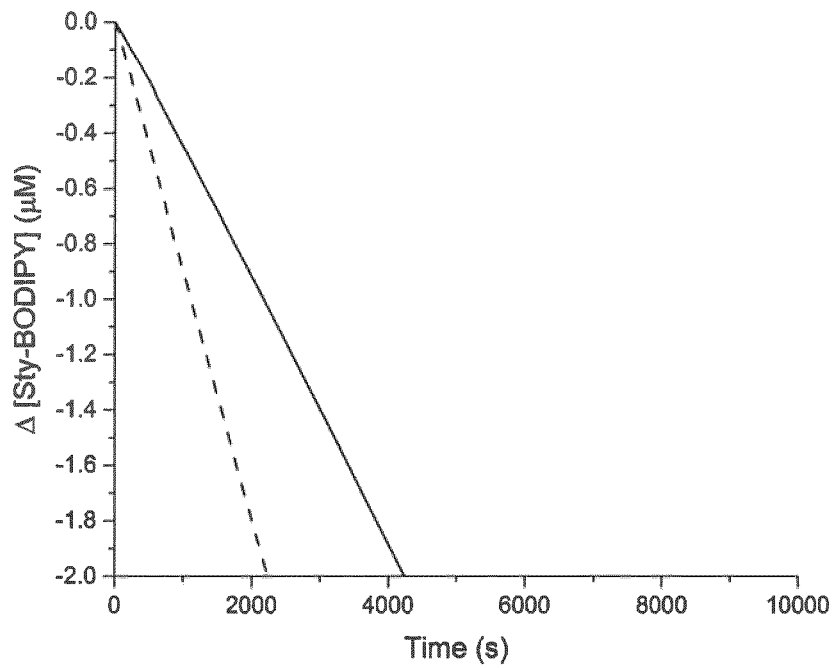
FIG. 23A Co-oxidations of 25% THF in aqueous buffer of pH 4 and Sty-BODIPY (10 μM), initiated with MPH (833 μM) at 37° C.: in the absence of an antioxidant (dashed line); and in the presence of an antioxidant, specifically, compound 2 μM of 24 (solid line). Reaction progress was monitored by absorbance at 562 nm ($\varepsilon$=132,261 $M^{-1}$ $cm^{-1}$).
Figure 23B:
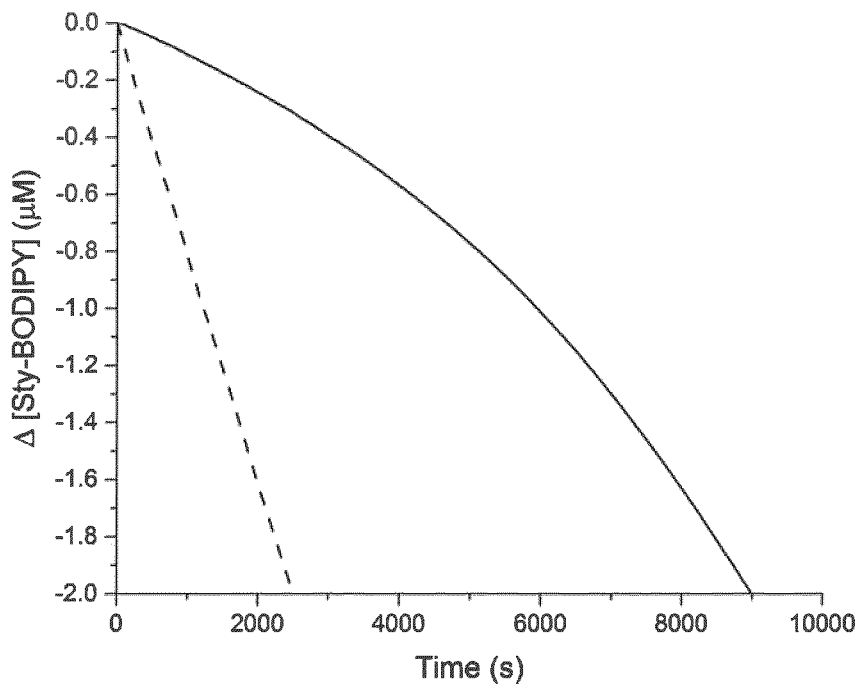
FIG. 23B Co-oxidations of 25% THF in aqueous buffer of pH 10 and Sty-BODIPY (10 μM), initiated with MPH (833 μM) at 37° C.: in the absence of an antioxidant (dashed line); and in the presence of an antioxidant, specifically, compound 2 μM of 24 (solid line). Reaction progress was monitored by absorbance at 562 nm ($\varepsilon$=132,261 $M^{-1}$ $cm^{-1}$).
Figure 24A:
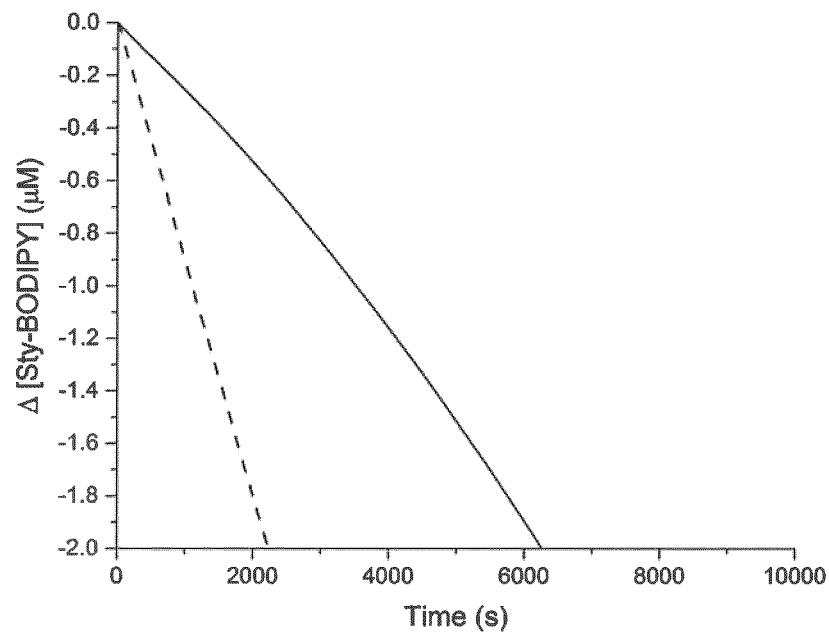
FIG. 24A Co-oxidations of 25% THF in aqueous buffer of pH 4 and Sty-BODIPY (10 μM), initiated with MPH (833 μM) at 37° C.: in the absence of an antioxidant (dashed line); and in the presence of an antioxidant, specifically, compound 2 μM of 25 (solid line). Reaction progress was monitored by absorbance at 562 nm ($\varepsilon$=132,261 $M^{-1}$ $cm^{-1}$).
Figure 24B:
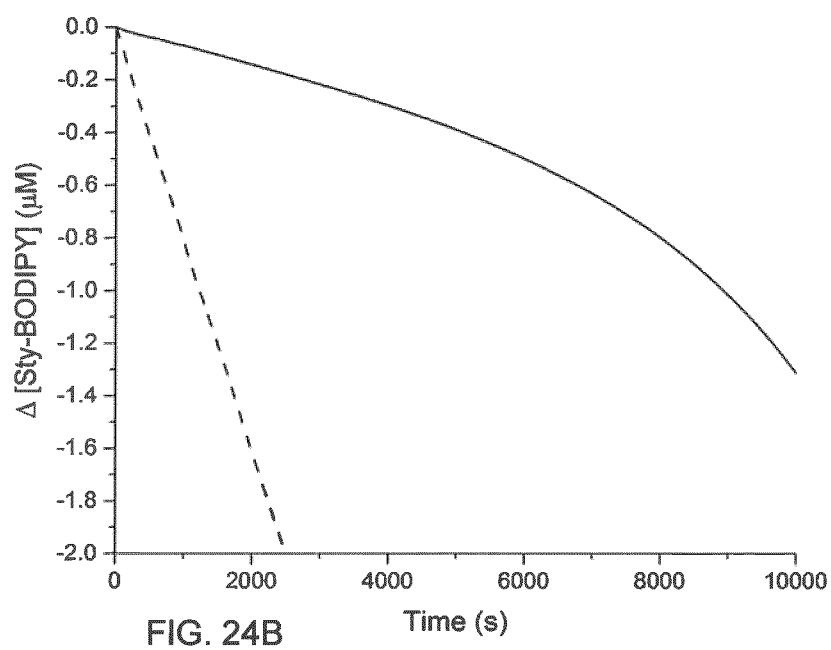
FIG. 24B Co-oxidations of 25% THF in aqueous buffer of pH 10 and Sty-BODIPY (10 μM), initiated with MPH (833 μM) at 37° C.: in the absence of an antioxidant (dashed line); and in the presence of an antioxidant, specifically, compound 2 μM of 25 (solid line). Reaction progress was monitored by absorbance at 562 nm ($\varepsilon$=132,261 $M^{-1}$ $cm^{-1}$).
Figure 25A:
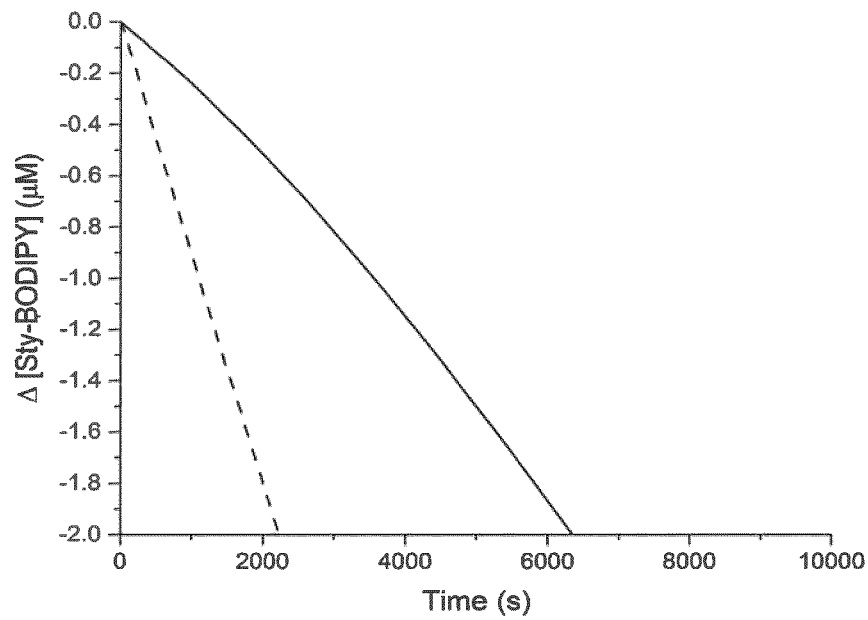
FIG. 25A Co-oxidations of 25% THF in aqueous buffer of pH 4 and Sty-BODIPY (10 μM), initiated with AAPH (833 μM) at 37° C.: in the absence of an antioxidant (dashed line); and in the presence of an antioxidant, specifically, compound 2 μM of 26 (solid line). Reaction progress was monitored by absorbance at 562 nm ($\varepsilon$=132,261 $M^{-1}$ $cm^{-1}$).
Figure 25B:
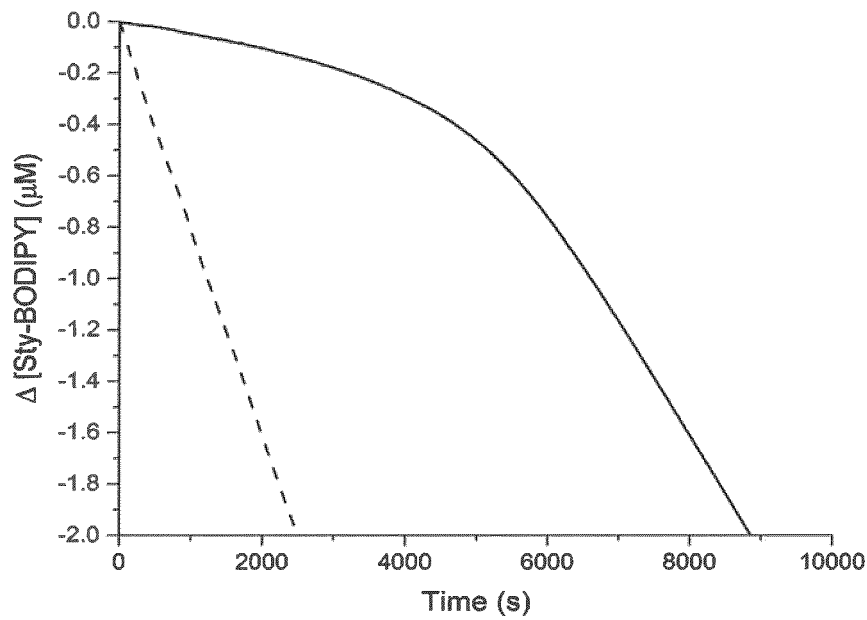
FIG. 25B Co-oxidations of 25% THF in aqueous buffer of pH 10 and Sty-BODIPY (10 μM), initiated with AAPH (833 μM) at 37° C.: in the absence of an antioxidant (dashed line); and in the presence of an antioxidant, specifically, compound 2 μM of 26 (solid line). Reaction progress was monitored by absorbance at 562 nm ($\varepsilon$=132,261 $M^{-1}$ $cm^{-1}$).

Referring to the figures, it has been demonstrated that the activity of heterocyclic antioxidants is enhanced in the presence of base. Specifically, hexadecane autoxidations are better inhibited by the specified antioxidant compounds in the presence of a representative base (2,4,6-tri-t-butylpyridine) than in its absence (see FIG. 2 I and FIGS. 2A and 2B, respectively). For clarity, these plots are shown individually in FIGS. 8, 9, 10, 11, 12 and 13. By comparison, added base did not impact the reactivity of a commercially available antioxidant, namely diphenylamine (see FIG. 7). FIGS. 14-17 show that reactivity enhancement resulted from an addition of base, in general, and is not specific to the 2,4,6-tri-t-butylpyridine used in several examples herein. Also included are results in the presence of primene 81R, cesium carbonate, or potassium carbonate. FIG. 18 shows that added acid does not affect the activity of commercially available antioxidant diphenylamine, which is consistent with the earlier observation that for a diphenylamine-inhibited autoxidation an addition of base had no effect. In contrast, FIG. 19 demonstrates that an addition of acid reduced the efficiency of a heterocyclic diarylamine. This result was consistent with the observation that the addition of base on an autoxidation inhibited by a heterocyclic diarylamine had a positive effect. FIGS. 20-25 are examples of autoxidations carried out in aqueous solution that show the same general phenomena, but now in pH-controlled media. At acidic pH, the heterocyclic diarylamines were less effective at inhibiting the autoxidation than they were at neutral pH, whereas only a comparatively small difference is observed for the diphenylamine.

In other embodiments, a base and antioxidant compound(s) are added to organic substrates such as biomass derived fuel components (biodiesel fuel) as an antioxidant to prevent oxidative degradation. Biodiesels include a variety of ester-based oxygenated fuels made from vegetable oils, fats, greases, or other sources of triglycerides. They are nontoxic and biodegradable substitute and supplement for petroleum diesel. Organic fuels, such as biodiesel, often include a wide variety of contaminants such that stability, especially by oxidative degradation, is a serious problem in these fuels, and such degradation often leads to gummy decomposition products.

Thus, encompassed within the scope of the invention are compositions of biodiesel fuels that include a base and antioxidant compound(s) wherein one or more of the ring atoms in one or both aryl groups are nitrogen. More particularly, in certain embodiments one or more of the atom(s) at the meta positions relative to the amine are nitrogen.

In some embodiments, a base and antioxidant compound(s) are used in conjunction with a lubricant or fuel to form a lubricating composition. In some embodiments, the lubricant includes a natural and/or a synthetic oil, oil derived from hydrocracking, hydrogenation, hydrofinishing, unrefined, refined and re-refined oils, and mixtures thereof, the lubricant having a viscosity appropriate for the particular lubricant application. In some embodiments the lubricating composition is useful as a crankcase lubricant. In other embodiments, the lubricating composition is useful for engines such as gasoline powered engines and diesel engines. In other embodiments, the lubricating composition is one which is conventionally employed in and/or adapted for use as power transmitting fluid such as automatic transmission fluids, tractor fluids, universal tractor fluids and hydraulic fluids, heavy duty hydraulic fluids, power steering fluids and the like. In yet other embodiments, gear lubricants, industrial oils, pump oils and other lubricating oil compositions including personal care products such as shampoo, lotions, etc. can also benefit from the incorporation therein of one or more of the compositions of the present invention.

In regard to the organic substrate to be protected from oxidation, the organic substrate can be present within the composition in an amount greater than about 40% by weight, greater than about 50% by weight, greater than about 60% by weight, greater than about 70%, greater than about 75% by weight, greater than about 80% by weight, greater than 85% by weight or greater than 90% by weight.

In some embodiments, the composition may further comprise one or more other antioxidants combined with one or more of the antioxidants of the current invention. In some embodiments the one or more other antioxidants include sterically hindered phenols. In some embodiments, the composition may further comprise other additives well known in the art. For example, "additives" as used herein in reference to viscosity improving materials, anti-wear agents, zinc salts, anti-deposition agents, hydrolytic stabilizers, friction modifiers, seal swell agents, anti-rust agents, foam suppressing agents, or pour point depressants.

In some embodiments, kits can be produced and distributed which incorporate a composition as described herein along with instructions for use.

Kits may be generated and comprise one or more antioxidant compounds and a base as described herein along with instructions for use. In one embodiment the instructions describe the means to prevent or reduce degradation of the organic substrate during storage, handling or use. Such kits may additionally comprise one or more "additives" including viscosity improving materials, anti-wear agents, zinc salts, anti-deposition agents, hydrolytic stabilizers, friction modifiers, seal swell agents, anti-rust agents, foam suppressing agents, or pour point depressants. Such kits may also comprise one or more traditional antioxidants in combination with a base and one or more diaryl antioxidant compounds as described herein. In one embodiment, one or more traditional antioxidants include sterically hindered phenols.

Kits may also be generated and comprise a base and one or more antioxidant compounds along with instructions for use of the compound(s) as an additive during synthesis of one or more organic substrates, to improve the stability or yield of the organic substrate during synthesis. Such kits may additionally comprise one or more monomers, dimers or trimers and appropriate solvents and/or buffers suitable for such synthesis of polymers from said monomers, dimers or trimers.

The following examples are given for illustrative purposes and are not intended to be limiting to the invention as disclosed herein.

Working Examples

Reagents were purchased from commercial suppliers and used without further purification, unless otherwise indicated. The diarylamines 1-4 were synthesized according to our previously published report (ref 1 from SI of JACS paper) with slight modifications. Diarylamine 5 was prepared described as described below and 6 was prepared exactly as previously described (ref 1 from SI of JACS paper). Column chromatography was carried out using flash silica gel (40-63 µm, 230-400 mesh). $^1$H and $^{13}$C NMR were recorded on a Bruker AVANCE spectrometer at 400 MHz and 100 MHz respectively, unless specified otherwise. High-resolution mass spectra were obtained on a Kratos Concept Tandem mass spectrometer.

Example 1. Synthetic Procedures (i) General alkylation Method for the Preparation of 5-bromo-N,N-dialkylaminopyri(mi)dines To a solution of 5-bromo-2-aminopyri(mi)dine (1.0 mmol) in dry THF (2 mL) at 50° C., NaH (2.2 mmol) was added slowly and the mixture was stirred until $H_2$ evolution ceased. Alkylbromide (2.1 mmol) was then added and the reaction was refluxed overnight. The reaction was cooled, quenched with MeOH and extracted with $Et_2O$. The combined organics were washed with brine and dried over $MgSO_4$. The oil obtained was passed through a plug of silica ($Et_2O$/hexanes) to obtain pure products.

5-Bromo-N,N-dihexylpyridin-2-amine (8)

Compound 8 was synthesized according to the general alkylation procedure listed above. 1-Bromohexane was used as the alkylbromide of choice. Yield: quantitative. Colourless Oil. $^1$H NMR (400 MHz; CDCl$_3$): δ 7.28 (s, 1H), 6.52 (d, J=9.1 Hz, 2H), 3.24 (t, J=7.7 Hz, 4H), 1.57 (t, J=6.1 Hz, 4H), 1.35 (m, 12H), 0.93 (t, J=6.7 Hz, 6H). $^{13}$C NMR (100 MHz; CDCl$_3$): δ 14.18, 22.83, 26.95, 27.19, 31.86, 51.27, 106.86, 113.42, 114.29, 131.88, 147.22, HRMS: m/z Calc: $C_{17}H_{29}BrN_2$: 340.15141 Found: 340.15159.

5-Bromo-N,N-dibutylpyrimidin-2-amine (9)

Compound 9 was synthesized according to the general alkylation procedure listed above. 1-Bromobutane was used as the alkylbromide of choice. Yield: 92%. Colourless Oil. $^1$H NMR (400 MHz; CDCl3): δ 8.20 (s, 2H), 3.46 (t, J=7.5 Hz, 4H), 1.57-1.49 (m, 4H), 1.30 (dt, J=14.6, 7.3 Hz, 5H), 0.90 (dd, J=7.2, 6.5 Hz, 7H). 13-C NMR (100 MHz; CDCl$_3$): δ 159.7, 157.6, 104.6, 77.4, 77.1, 76.7, 47.8, 29.8, 20.2, 14.0, HRMS: m/z Calc: $C_{12}H_{20}BrN_3$: 285.08406 Found: 285.08412.

5-Bromo-N,N-dihexylpyrimidin-2-amine (10)

Compound 10 was synthesized according to the general alkylation procedure listed above. 1-Bromohexane was used as the alkylbromide of choice. Yield: 92%. Colourless Oil. $^1$H NMR. (400 MHz; CDCl3): δ 8.24 (s, 2H), 3.48 (t, J=7.6 Hz, 4H), 1.57 (s, 5H), 1.30 (t, J=3.3 Hz, 12H), 0.89 (d, J=2.5 Hz, 6H). $^{13}$C NMR (100 MHz; CDCl$_3$): δ 159.8, 157.7, 104.7, 48.2, 31.8, 27.6, 26.8, 22.8, 14.2, HRMS: m/z Calc: $C_{16}H_{28}BrN_3$: 340.14666 Found: 340.14668.

5-Bromo-N,N-dimethylpyridin-2-amine (14)

Compound 14 was synthesized according to the general alkylation procedure listed above. Bromomethane was used as the alkylbromide of choice. Yield: 88%. White solid. $^1$H NMR (CDCl3, 400 MHz) δ ppm 8.12 (d, J=2.3 Hz, 1H), 7.60 (dd, J=9.2, 2.6 Hz, 1H), 6.61 (d, J=9.4 Hz, 1H), 2.99 (s, 6H). $^{13}$C NMR (CDCl$_3$, 100 MHz) δ ppm 160.3, 153.1, 147.2, 110.8, 104.2, 38.3. HRMS: m/z Calc: $C_7H_9BrN_2$: 199.9949, found 199.9946.

5-Bromo-N,N-dimethylpyrimidin-2-amine (15)

Compound 15 was synthesized according to the general alkylation procedure listed above. Bromomethane was used as the alkylbromide of choice. Yield: 82%. White solid. $^1$H NMR (CDCl$_3$, 400 MHz) δ ppm 8.29 (s, 2H), 3.16 (s, 6H). $^{13}$C NMR (CDCl$_3$, 100 MHz) δ ppm 160.5, 157.7, 105.1, 37.3. m.p. 102-103° C. HRMS: m/z Calc: $C_6H_8BrN_3$: 200.9902, found 200.9910.

5-Bromo-N,N-diethylpyrimidin-2-amine (16)

Compound 16 was synthesized according to the general alkylation procedure listed above. Bromoethane was used as the alkylbromide of choice. Yield: 87%. White solid. $^1$H NMR (CDCl$_3$, 400 MHz) δ ppm 8.45 (s, 2H), 3.16 (q, J=7.4 Hz, 4H), 0.99 (t, J=7.3 Hz, 6H). $^{13}$C NMR (CDCl$_3$, 100 MHz) δ ppm 160.8, 159.6, 107.8, 45.2, 11.7. HRMS: m/z Calc: $C_8H_{12}BrN_3$: 229.0215, found 229.0211.

5-Bromo-N,N-dioctylpyrimidin-2-amine (32)

Compound 32 was synthesized according to the general alkylation procedure listed above. 1-bromooctane was used as the alkylbromide of choice. Yield: 89%. Yellow Oil. $^1$H-NMR (400 MHz; CDCl3): δ 8.26 (s, 2H), 3.50 (t, J=7.6 Hz, 4H), 1.61-1.59 (m, 4H), 1.32-1.29 (m, 20H), 0.90 (t, J=6.9 Hz, 6H).

4-bromo-tert-butylbenzene (17)

To a solution of tert-butylbenzene (1.0 mmol) in $CH_2Cl_2$ (0.15 mL) at 0° C. under argon was added Iron (0.03 mmol). Bromine (1.05 mmol) was added dropwise and the solution was stirred overnight. The reaction was extracted with 1.0M NaOH and (3×) DCM. The organics were combined, dried over $MgSO_4$ and the solvent was removed under reduced pressure. The crude product was then distilled under vacuum at ca. 120° C. Colourless Oil. Yield: 80%

4-tert-butylaniline (18)

To a sealed tube were added 17 (1.0 mmol), CuI (0.2 mmol), L-proline (0.4 mmol), and $K_2CO_3$ (1.5 mmol). The flask was filled with argon before DMSO (1.5 mL) and Water (1.0% v/v) was added. After a 10 minutes of stirring, ammonium hydroxide (3.0 mmol) was added and the reaction was heated to 90° C. until completion, as determined by TLC (~12 hours). The reaction was cooled, quenched with water, and extracted with $Et_2O$. The combined organics were washed twice with water, washed with brine, and dried over $MgSO_4$. The crude mixture was passed through a silica plug (70% EtOAc/Hexanes eluent) to afford pure product. Colourless Oil. Yield: 84%.

5-Bromo-2-hexylpyrimidine (11)

n-Hexylmagnesium bromide was prepared prior to use. Mg (1.0 mmol) in dry THF was activated 4 times with 12. n-Hexyl bromide (1.0 mmol) in dry THF (10 mL) was added slowly to maintain the solution near reflux. After addition was complete the reaction was heated to 60° C. for 1 hour. $ZnCl_2$ (1.25 mmol) solution was added dropwise to Hexylmagnesiumbromide (1.0 mmol) in THF (12.5 mL) and stirred for 10 minutes. 5-Bromo-2-iodopyrimidine (0.5 mmol) and catalytic Pd(PPh$_3$)$_4$ was added and stirred overnight. The reaction quenched with water, and extracted with Et$_2$O. The combined organics were washed with brine, and dried over MgSO$_4$. Column chromatography (10% Et$_2$O/hexanes eluent) afforded pure products. Yield: 61%. White Powder. $^1$H NMR (400 MHz; CDCl$_3$): δ 8.69 (s, 2H), 2.90 (t, J=7.7 Hz, 2H), 1.78 (dt, J=14.7, 7.5 Hz, 2H), 1.31 (dd, J=5.9, 3.6 Hz, 7H), 0.87 (t, J=7.0 Hz, 3H). $^{13}$C NMR (100 MHz; CDCl$_3$): δ 170.0, 157.7, 117.7, 39.0, 31.7, 29.1, 28.7, 22.7, 14.2, HRMS: m/z Calc: C$_{10}$H$_{15}$BrN$_2$: 242.04186 Found: 242.04194.

Differently substituted 5-bromo-2-alkyl pyrimidines could be prepared through an analogous procedure starting from the appropriate alkyl halide.

2-Hexylpyrimidin-5-amine (19)

Compound 19 was prepared using the same procedure as compound 18 except compound 11 was used as the starting material instead of compound 17. Yield: 58% off white solid. $^1$H NMR (CDCl$_3$, 400 MHz) δ ppm 8.13 (s, 2H), 6.34 (brs, 2H), 2.81 (t, J=7.7 Hz, 2H), 1.73 (qt, J=7.7 Hz, 2H), 1.33-1.27 (m, 6H), 0.84 (t, J=7.0 Hz, 3H). $^{13}$C NMR (CDCl$_3$, 100 MHz) δ ppm 161.924, 143.401, 137.726, 38.409, 31.621, 28.997, 28.941, 22.508, 14.006. m.p. 107-108° C. HRMS: m/z Calc: C$_{10}$H$_{17}$N$_3$: 179.1423, found 179.1407.

Differently substituted 2-alkylpyrimidine-5-amines could be prepared through an analogous procedure starting from the appropriate 5-bromo-2-alkylpyrimidine.

5-Benzylamino-N,N-dibutylpyrimidin-2-amine (12)

To a sealed tube was added 9 (1.0 mmol), CuI (0.2 mmol), L-proline (0.4 mmol), and K$_2$CO$_3$ (1.5 mmol The flask was backfilled with argon before DMSO (1.5 mL) and water (1.0% v/v) was added. After a few minutes of stirring, benzylamine (1.8 mmol) was added and the reaction was heated to 80° C. until completion, as determined by TLC. The reaction was cooled, quenched with water, and extracted with Et$_2$O. The combined organics were washed twice with water, washed with brine, and dried over MgSO$_4$. Column chromatography (40% Et$_2$O/hexanes eluent) afforded pure products. The compound was recrystallized from hexanes to analytical purity. Yield: 83%. Yellow Needles. $^1$H NMR (400 MHz; CDCl$_3$): δ 7.91 (s, 2H), 7.35-7.26 (m, 5H), 4.23 (s, 2H), 3.47 (t, J=7.5 Hz, 4H), 1.59-1.51 (m, 4H), 1.33 (dq, J=15.1, 7.5 Hz, 4H), 0.93 (t, J=7.3 Hz, 6H). $^{13}$C NMR (100 MHz; CDCl$_3$): δ 157.3, 145.1, 139.3, 132.5, 128.8, 127.72, 127.52, 77.5, 77.2, 76.8, 50.1, 47.8, 30.3, 20.4, 14.2, HRMS: m/z Calc: C$_{23}$H$_{36}$N$_4$: 368.29400 Found: 368.29395.

5-Benzylamino-N,N-diethylpyrimidin-2-amine (30)

Compound 30 was synthesized to a similar procedure as Compound 12 except Compound 16 was used instead of 9. Yield: 72%. Yellow solid. $^1$H NMR (CDCl$_3$, 400 MHz) δ ppm 7.93 (s, 2H), 7.37-7.27 (m, 5H), 4.24 (s, 2H), 3.55 (q, J=7.0 Hz, 4H), 3.41 (brs, 1H), 1.15 (t, J=7.0 Hz, 6H). $^{13}$C NMR (CDCl3, 100 MHz) δ ppm 156.598, 145.035, 139.023, 132.458, 128.652, 127.538, 127.362, 49.867, 41.883, 13.202. m.p. 89-90° C. HRMS: m/z Calc: C$_{15}$H$_{20}$N$_4$: 256.1688, found 256.1668.

N$^2$,N$^2$-Dibutylpyrimidine-2,5-diamine (13)

To a solution of 12 (1.0 mmol) in degassed MeOH (5 mL) were added 10% Pd/C (10 wt %) and ammonium formate (3.0 mmol). The flash was backfilled with argon and the solution was heated to reflux until completion, as determined by TLC. When complete, the solution was cooled and filtered through a pad of celite. The solvent was evaporated and the resulting solid was re-dissolved in a 40% Et$_2$O/hexanes solution. The precipitate formed was filtered off through another pad of celite and washed with ether. The solvent was evaporated to obtain the desired compound without any residual ammonium formate. No further purification was attempted because of oxidative instability and difficulty associated with chromatographing this compound.

N$^2$,N$^2$-Diethylpyrimidine-2,5-diamine (31)

To a solution of 30 (1.0 mmol) in degassed MeOH (5 mL) were added 10% Pd/C (10 wt %) and ammonium formate (3.0 mmol). The flash was backfilled with argon and the solution was heated to reflux until completion, as determined by TLC. When complete, the solution was cooled and filtered through a pad of celite. The solvent was evaporated and the resulting solid was re-dissolved in a 40% Et$_2$O/hexanes solution. The precipitate formed was filtered off through another pad of celite and washed with ether. The solvent was evaporated to obtain the desired compound without any residual ammonium formate. No further purification was attempted because of oxidative instability and difficulty associated with chromatographing this compound.

(ii) General Method for the Preparation of Diarylamines

To a flame-dried Schlenk flask were added Pd$_2$dba$_3$ (0.01 mmol) and BippyPhos (0.04 mmol). The flask was evacuated and backfilled with argon before tert-amylalcohol (1 mL) was added, followed by KOH (1.5 mmol) and H$_2$O (1.0% v/v) and the solution was stirred for 20 minutes. Aryl bromide (1.0 mmol) and arylamine (1.1 mmol) were then added, and the reaction was heated to 110° C. Once complete, the mixture was concentrated under vacuum and loaded on a silica column. Column chromatography (Et$_2$O/hexanes containing 1-5% Et$_3$N depending on substrate) afforded pure products.

N$^2$,N$^2$-Dibutyl-N$^5$-(6-(dihexylamino)pyridin-3-yl)pyrimidine-2,5-diamine (1)

Compound 1 was synthesized according to the general preparation of diarylamines: Compound 8 was used as the arylbromide and Compound 13 was used as the arylamine. Yield: 67%. Brown Oil. $^1$H NMR (300 MHz; CDCl$_3$): δ 8.09 (s, 2H), 7.83 (d, J=2.7 Hz, 1H), 7.07 (dd, J=9.0, 2.9 Hz, 1H), 6.35 (d, J=8.9 Hz, 1H), 4.75 (s, 1H), 3.58 (q, J=7.0 Hz, 4H), 3.36 (t, J=7.6 Hz, 4H), 1.57-1.52 (m, 4H), 1.29-1.26 (m, 20H), 1.17 (t, J=7.0 Hz, 6H), 0.87 (t, J=6.7 Hz, 6H). $^{13}$C NMR (75 MHz; CDCl$_3$): δ 157.9, 154.2, 151.0, 138.9, 130.6, 129.0, 128.8, 106.0, 49.1, 42.2, 32.0, 29.7, 29.5, 27.9, 27.3, 22.8, 14.2, 13.3, HRMS: m/z Calc: C$_{29}$H$_{50}$N$_6$: 482.40970 Found: 482.40988.

N$^2$,N$^2$-Dibutyl-N$^5$-(2-(dibutylamino)pyrimidin-5-yl)pyrimidine-2,5-diamine (2)

Compound 2 was synthesized according to the general preparation of diarylamines: Compound 9 was used as the arylbromide and Compound 13 was used as the arylamine. Yield: 65%. Yellow Powder. $^1$H NMR (300 MHz; CDCl$_3$): δ 7.95 (s, 4H), 3.47 (t, J=7.5 Hz, 8H), 1.60-1.50 (m, 9H), 1.33 (dt, J=15.0, 7.4 Hz, 9H), 0.92 (t, J=7.3 Hz, 12H). $^{13}$C NMR (75 MHz; CDCl$_3$): δ 157.7, 147.0, 129.4, 47.8, 30.2, 20.4, 14.2, HRMS: m/z Calc: C$_{24}$H$_{41}$N$_7$: 427.34234 Found: 427.34222.

N$^2$,N$^2$-Dihexyl-N$^5$-phenylpyridine-2,5-diamine (3)

Compound 3 was synthesized according to the general preparation of diarylamines: Compound 8 was used as the arylbromide and aniline was used as the arylamine. Yield: 74%. Brown Oil. $^1$H NMR (400 MHz; CDCl$_3$): δ 8.03 (d, J=2.7 Hz, 1H), 7.31 (dd, J=9.0, 2.8 Hz, 1H), 7.19-7.15 (m, 2H), 6.78-6.75 (m, 3H), 6.43 (d, J=9.0 Hz, 1H), 5.25 (s, 1H), 3.42 (t, J=7.7 Hz, 4H), 1.62-1.56 (m, 4H), 1.35-1.32 (m, 12H), 0.90 (t, J=6.8 Hz, 6H). $^{13}$C NMR (100 MHz; CDCl$_3$): δ 14.22, 22.86, 27.01, 27.83, 31.94, 49.10, 105.76, 114.26, 118.71, 126.69, 129.40, 134.36, 144.46, 147.00, 155.58, HRMS: m/z Calc: C$_{23}$H$_{35}$N$_3$: 353.28310 Found: 353.34289.

N$^2$,N$^2$-Dihexyl-N$^5$-phenylpyrimidine-2,5-diamine (4)

Compound 4 was synthesized according to the general preparation of diarylamines: Compound 10 was used as the arylbromide and aniline was used as the arylamine. Yield: 81%. Brown Oil. $^1$H NMR (400 MHz; CDCl$_3$): δ 8.22 (s, 2H), 7.20-7.16 (m, 2H), 6.79 (t, J=7.3 Hz, 1H), 6.72 (d, J=7.6 Hz, 2H), 5.13 (s, 1H), 3.54 (t, J=7.6 Hz, 4H), 1.63-1.58 (m, 4H), 1.33 (d, J=3.7 Hz, 12H), 0.90 (t, J=6.6 Hz, 6H). 13-C NMR (100 MHz; CDCl$_3$): δ 159.5, 155.4, 146.8, 129.5, 124.9, 119.1, 114.0, 48.2, 31.9, 27.9, 26.9, 22.8, 14.2, HRMS: m/z Calc: C$_{22}$H$_{34}$N$_4$: 354.27835 Found: 354.27903.

N$^2$,N$^2$-Dibutyl-N$^5$-(2-hexylpyrimidin-5-yl)pyrimidine-2,5-diamine (5)

Compound 5 was synthesized according to the general preparation of diarylamines: Compound 11 was used as the arylbromide and Compound 13 was used as the arylamine. Yield: 84%. Yellow Powder. $^1$H NMR (400 MHz; CDCl$_3$): δ 8.19 (s, 2H), 8.15 (s, 2H), 5.23-5.16 (m, 1H), 3.53 (t, J=7.5 Hz, 4H), 2.83 (t, J=7.7 Hz, 2H), 1.74 (quintet, J=7.1 Hz, 2H), 1.59 (quintet, J=7.3 Hz, 4H), 1.37-1.29 (m, 10H), 0.94 (t, J=7.3 Hz, 6H), 0.86-0.84 (m, 3H). 13-C NMR (100 MHz; CDCl$_3$): δ 162.4, 159.8, 155.4, 142.7, 138.6, 123.1, 48.0, 38.6, 31.8, 30.0, 29.18, 29.11, 22.7, 20.4, 14.20, 14.16, HRMS: m/z Calc: C$_{22}$H$_{36}$N$_6$: 384.30015 Found: 384.30997.

Bis(2-heptylpyrimidin-5-yl)amine (6)

Compound 6 was synthesized according to the general preparation of diarylamines: A derivative of compound 11 with heptyl chain was used as the arylbromide and a derivative of Compound 19 with heptyl chain was used as the arylamine. Yield: 81% white solid. $^1$H NMR (CDCl$_3$, 400 MHz) δ ppm 8.48 (s, 4H), 5.58 (brs, 1H), 2.92 (t, J=7.6 Hz, 4H), 1.84-1.76 (m, 4H), 1.36-1.28 (m, 16H), 0.87 (t, J=6.4 Hz, 6H). $^{13}$C NMR (CDCl$_3$, 100 MHz) δ ppm 165.473, 146.585, 134.057, 38.664, 31.743, 29.316, 29.108, 28.809, 22.627, 14.071. m.p. 103-104° C. HRMS: m/z Calc: C$_{22}$H$_{35}$N$_5$: 369.2893, found 369.2892.

N$^5$-(4-(tert-butyl)phenyl)-N$^2$,N$^2$-dioctylpyrimidine-2,5-diamine (20)

Compound 20 was synthesized according to the general preparation of diarylamines: Compound 32 was used as the arylbromide and Compound 18 was used as the arylamine. $^1$H-NMR (300 MHz; CDCl$_3$): δ 8.26 (s, 2H), 7.26 (d, J=8.7 Hz, 2H), 6.73 (d, J=8.7 Hz, 2H), 5.30 (s, 1H), 3.61 (t, J=7.5 Hz, 4H), 1.69 (br, 4H), 1.35 (br, J=13.2 Hz, 29H), 0.93 (t, J=6.7 Hz, 6H). $^{13}$C NMR (76 MHz; CDCl$_3$): δ 159.1, 154.7, 144.1, 141.8, 126.2, 125.5, 113.8, 48.1, 34.0, 31.9, 31.5, 29.6, 29.4, 27.9, 27.2, 22.7, 14.2. HRMS: m/z Calc: C$_{30}$H$_{50}$N$_4$: 466.40355, found 466.40245.

N$^2$,N$^2$-dimethyl-N$^5$-phenylpyrimidine-2,5-diamine (22)

Compound 22 was synthesized according to the general preparation of diarylamines: Compound 15 was used as the arylbromide and aniline was used as the arylamine. Yield: 93% yellow solid. $^1$H NMR (CDCl$_3$, 400 MHz) δ ppm 8.26 (s, 2H), 7.21-7.16 (m, 2H), 6.80 (tt, J=7.3, 1.0 Hz, 1H), 6.73-6.70 (m, 2H), 5.23 (brs, 1H), 3.20 (s, 6H). $^{13}$C NMR (CDCl$_3$, 100 MHz) δ ppm 159.913, 154.978, 146.353, 129.380, 125.268, 119.080, 113.893, 37.379. m.p. 111-112° C. HRMS: m/z Calc: C$_{12}$H$_{14}$N$_4$: 214.1218, found 214.1197.

N$^5$-(4-(tert-butyl)phenyl)-N$^2$,N$^2$-dimethylpyrimidine-2,5-diamine (23)

Compound 23 was synthesized according to the general preparation of diarylamines: Compound 15 was used as the arylbromide and Compound 18 was used as the arylamine. Yield: 74%. Yellow Solid. $^1$H NMR (DMSO-d6, 400 MHz) δ ppm 8.22 (s, 2H), 7.46 (s, 1H), 7.16-7.14 (m, 2H), 6.69-6.67 (m, 2H), 3.10 (d, J=1.1 Hz, 6H), 1.22 (s, 9H). $^{13}$C NMR (CDCl$_3$, 100 MHz) δ ppm 152.1, 144.1, 142.9, 141.8, 132.8, 128.5, 119.7, 38.8, 34.6, 31.0. HRMS: m/z Calc: C$_{16}$H$_{22}$N$_4$: 270.1844, found 270.1845.

N$^2$,N$^2$-dimethyl-N$^5$-phenylpyridine-2,5-diamine (24)

Compound 24 was synthesized according to the general preparation of diarylamines: Compound 14 was used as the arylbromide and aniline was used as the arylamine. Yield: 94% yellow solid. $^1$H NMR (CDCl$_3$, 400 MHz) δ ppm 8.07 (d, J=2.6 Hz, 1H), 7.36 (dd, J=8.9, 2.7 Hz, 1H), 7.20-7.16 (m, 2H), 6.80-6.76 (m, 3H), 6.54 (d, J=9.3 Hz, 1H), 5.35 (brs, 1H), 3.09 (s, 3H). $^{13}$C NMR (CDCl$_3$, 100 MHz) δ ppm 156.731, 146.475, 143.649, 133.943, 129.272, 127.533, 118.801, 114.256, 106.092, 38.450. m.p. 134-136° C. HRMS: m/z Calc: C$_{12}$H$_{15}$N$_3$: 213.1266, found 213.1185.

N$^5$-(4-(tert-butyl)phenyl)-N$^2$,N$^2$-dimethylpyridine-2,5-diamine (25)

Compound 25 was synthesized according to the general preparation of diarylamines: Compound 14 was used as the arylbromide and Compound 18 was used as the arylamine. Yield: 68%. Brown solid. $^1$H NMR (DMSO-d6, 400 MHz) δ ppm 8.22 (s, 2H), 7.46 (s, 1H), 7.16-7.14 (m, 2H), 6.69-6.67 (m, 2H), 3.10 (d, J=1.1 Hz, 6H), 1.22 (s, 9H). $^{13}$C NMR (CDCl$_3$, 100 MHz) δ ppm 148.9, 142.1, 140.9, 135.1, 134.1, 127.5, 122.8, 119.7, 110.5, 38.5, 34.0, 31.6. HRMS: m/z Calc: C$_{17}$H$_{23}$N$_3$: 269.1892, found 269.1896.

N$^5$-(6-(dimethylamino)pyridin-3-yl)-N$^2$,N$^2$-diethylpyrimidine-2,5-diamine (26)

Compound 26 was synthesized according to the general preparation of diarylamines: Compound 14 was used as the arylbromide and Compound 31 was used as the arylamine. Yield: 91% metallic green solid. $^1$H NMR (CDCl$_3$, 400

MHz) δ ppm 8.11 (s, 2H), 7.87 (d, J=2.8 Hz, 1H), 7.10 (dd, J=2.8, 8.8 Hz, 1H), 6.46 (d, J=8.8 Hz, 1H), 4.74 (brs, 1H), 3.58 (q, J=7.0 Hz, 4H), 3.03 (s, 3H), 1.18 (t, J=7.0 Hz, 6H). $^{13}$C NMR (d6-acetone, 100 MHz) δ ppm 159.481, 157.140, 152.018, 139.499, 134.195, 131.236, 129.480, 108.020, 43.473, 39.636, 14.533. m.p. 102-103° C. HRMS: m/z Calc: $C_{15}H_{22}N_6$: 286.1906, found 286.1907.

Figures 2C, 2D:
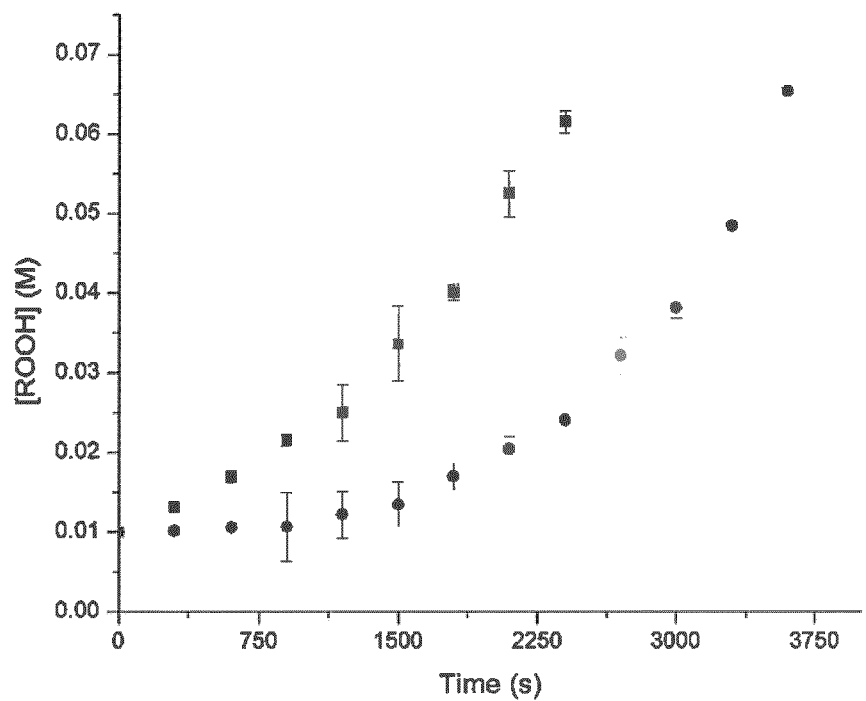
FIG. 2C shows data from an uninhibited autoxidation and one inhibited with diarylamine 4. Specifically, hydroperoxide formation in the autoxidation of n-hexadecane at 160° C. was initiated by 10 mM tetralin hydroperoxide (■), and with an added 40 µM of 4 (♦).
FIG. 2D shows an analogous experiment to that of FIG. 2C, with the difference that this graph includes data in the absence of tetralin hydroperoxide initiator.
Figure 2E:
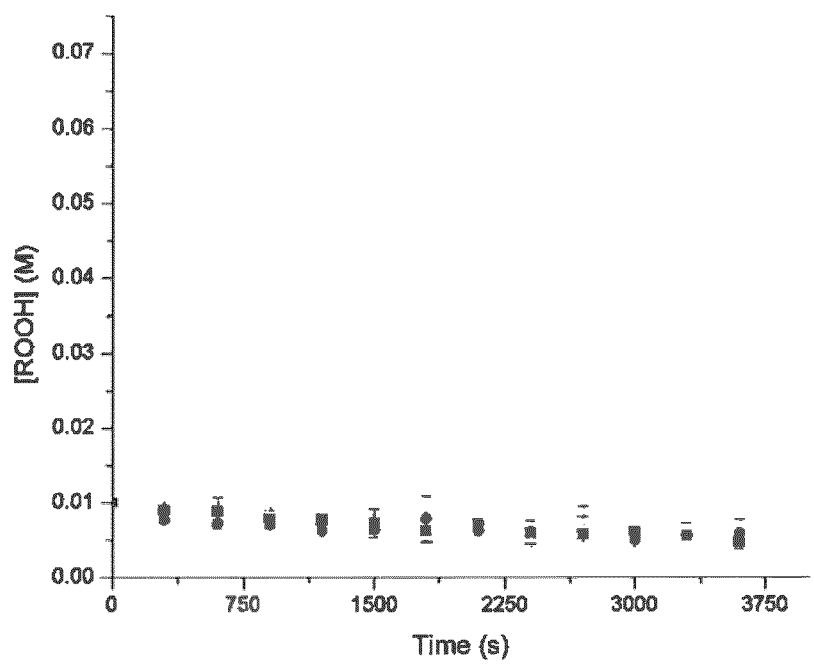
FIG. 2E shows an analogous experiment to that of FIG. 2C, in the presence of 10 mM tetralin hydroperoxide (■) and with an added 40 µM of 4 (♦), but in the absence of $O_2$.
Figure 5A:
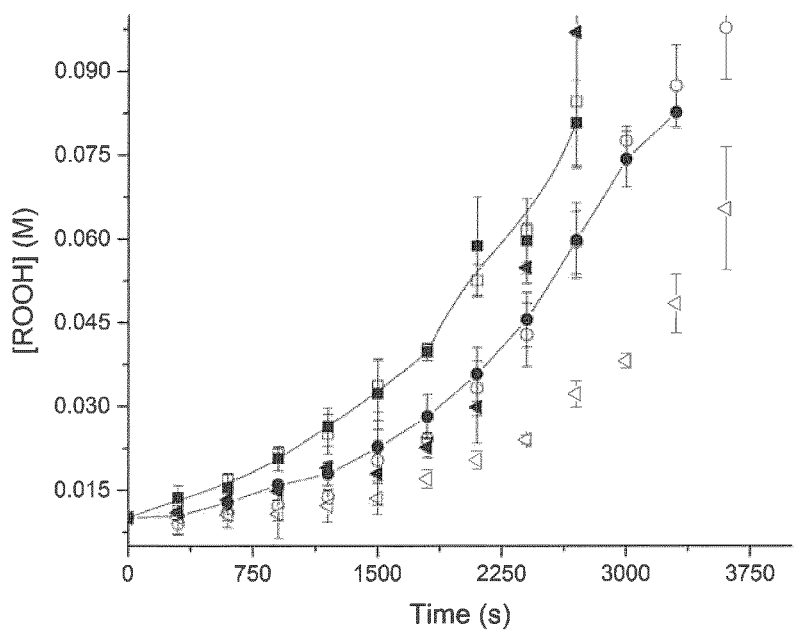
FIG. 5A graphically presents data collected during hydroperoxide formation in the autoxidation of hexadecane at 160° C. initiated by 10 mM tetralin hydroperoxide (■) and inhibited by 40 µM of either 7 (●) or 4 (◄) in the presence of palmitic acid (1 mM). Empty symbols depict autoxidations carried out in the absence of acid.
Figure 5B:
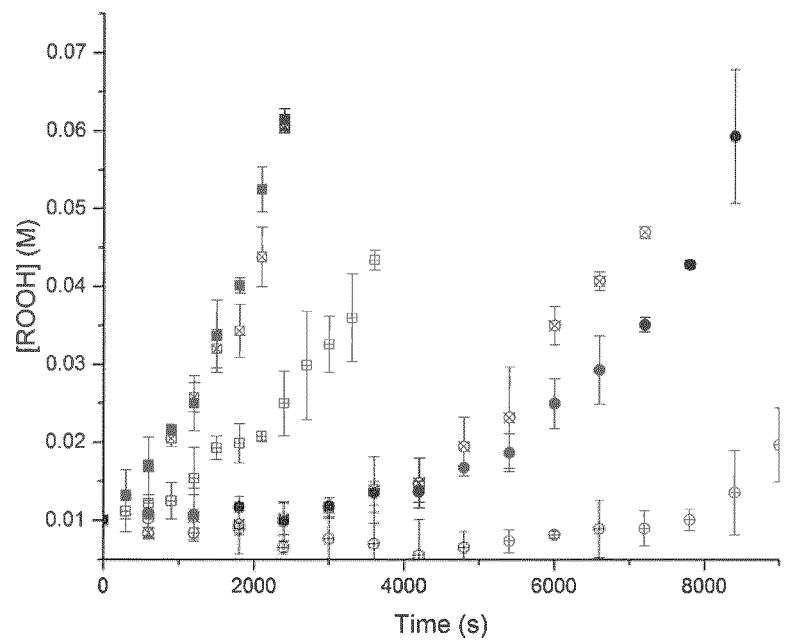
FIG. 5B graphically presents data collected during hydroperoxide formation in the autoxidation of n-hexadecane at 160° C. initiated by 10 mM tetralin hydroperoxide in the presence of 1.0 mM TTBP (■), 1.0 mM $Cs_2CO_3$ (⊞), and ca. 1.0 mM Primene 81-R (molecular weight estimated at 190 g/mol) (⊠) and inhibited by 40 µM of 4 in the presence of 1.0 mM TTBP (♦), 1.0 mM $Cs_2CO_3$ (⊕), and ca. 1.0 mM DOW PRIMENE™ 81-R (⊗).

Example 2. Hexadecane Autoxidations n-Hexadecane (100 mL) was thoroughly degassed with argon and heated to 160° C. while argon was continuously bubbled through the liquid. Once the temperature stabilized, 0.04 mmol of inhibitor (1-7) and 164 mg (1.0 mmol) of tetralin hydroperoxide were added to the solution and the flow of argon was replaced with O2. For those experiment where acid or base was present, as noted in the figure captions, they were also added at this point. Aliquots (0.5 mL) were removed every 5 minutes, and allowed to cool to room temperature for analysis. Four duplicates (30 µL) of each sample were loaded into separate wells of a 96-well microplate and the automated reagent dispenser of the microplate reader was used to dilute each sample with tert-amyl alcohol (200 µL) and a solution of fluorogenic phosphine dye solution (20 µL of a 250 µM stock solution in acetonitrile) immediately before reading. The plate was stirred for 8 seconds, allowed to rest for 2 more seconds, and the fluorescence of each well was measured every second for 60 seconds (absorption at 340; emission at 425). The concentration of hydroperoxide was determined from the rate of phosphine oxidation using the rate constant for the reaction of the dye with secondary hydroperoxides in tert-amyl alcohol ($k=1.2$ $M^{-1}s^{-1}$) assuming pseudo-first-order kinetics. See sample data from an uninhibited autoxidation and one inhibited with diarylamine 4 alongside analogous experiments in the absence of the initiator tetralin hydroperoxide, or $O_2$ (FIGS. 2C-E). Further results are presented in FIGS. 7 to 17 for hexadecane autoxidations and FIGS. 18 and 19 for tetralin autooxidations in the presence and absence of antioxidants, and at varying pH. FIGS. 14-17 correspond to hexadecane autoxidations carried out for diarylamine 4 in the presence of four different bases. FIGS. 7-13 correspond to hexadecane autoxidations carried out for compounds 1-7 and 20 in the presence and absence of a base, specifically, 2,4,6-tri-tert-butylpyridine. FIG. 5A corresponds to hexadecane autoxidations carried out for diarylamine 4 and 7 in the presence and absence of palmitic acid.

Example 3. Diarylamine Stability to Hydroperoxides

Figure 2F:
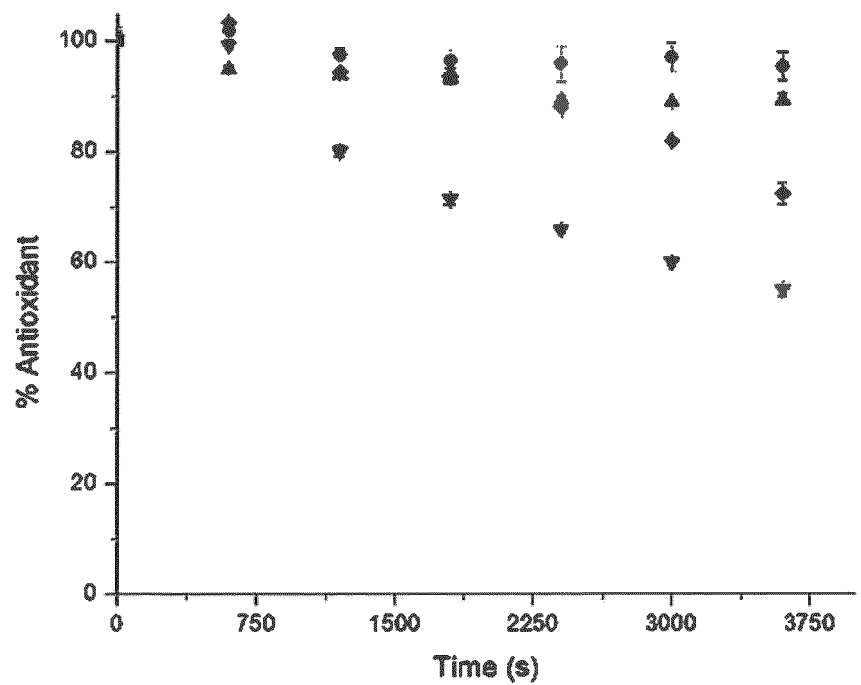
FIG. 2F graphically shows data regarding decomposition of diarylamines at 160° C. in the hexadecane in the presence of 10 mM tetralin hydroperoxide under argon: 1 (▼), 2 (♦), 3 (▲) and 7 (●).
Figure 2G:
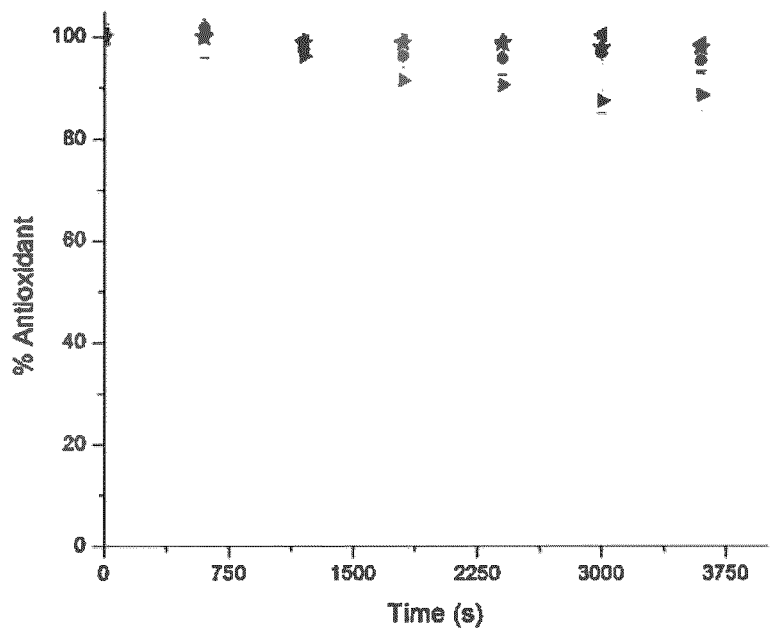
FIG. 2G graphically shows data regarding decomposition of diarylamines at 160° C. in the hexadecane in the presence of 10 mM tetralin hydroperoxide under argon: 4 (◄), 5 (►), 6 (★) and 7 (●).
Figure 2H:
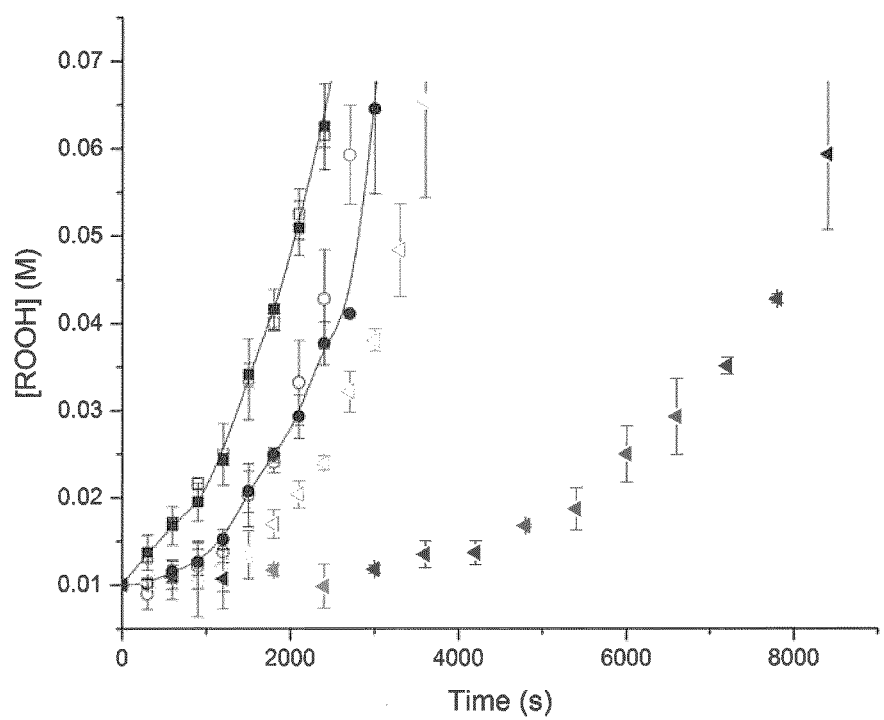
FIG. 2H graphically shows hydroperoxide formation in the autoxidation of n-hexadecane at 160° C. initiated by 10 mM tetralin hy-droperoxide (■) and inhibited by 40 µM of either 4 (◄) or 7 (♦) in the presence of 2,4,6-tri-tert-butylpyridine (1 mM); empty symbols correspond to the data in FIG. 2A-B (in the absence of TTBP).
Figure 2I:
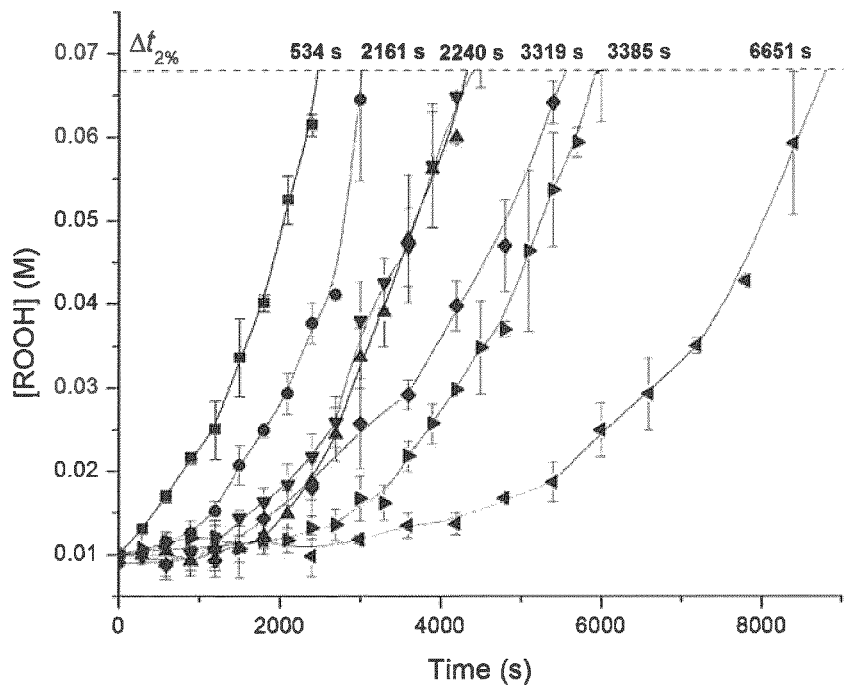
FIG. 2I graphically shows hydroperoxide formation in the autoxidation of n-hexadecane at 160° C. initiated by 10 mM tetralin hydroperoxide (■) and inhibited by 40 µM of 1 (▼), 2 (♦), 3 (▲), 4 (◄), 5 (►) or 7 (●), in the presence of TTBP (1 mM); the delay in the time required to reach [ROOH]=2% (=68 mM) in the presence of each of 1-5 and 7 is given as $\Delta t_{2\%}$.

Degassed n-hexadecane (1.0 mL) was added to 2.5 mmol of diarylamines 1-7 that were weighed into a glass vial under argon. A magnetic Teflon coated stir bar was added, the vial was capped with a rubber septum and fitted with an argon balloon. The suspension was stirred for a few minutes to dissolve the solid. The vial was then placed in a heating block at 160° C. for 30 seconds before 10 µL of a 1.0 M solution of tetralin hydroperoxide solution in ethyl acetate was added. The solution was stirred for 30 seconds and the first sample was taken. Subsequent 100 µL aliquots were removed at regular intervals and added to 900 µL of a 2.2 mM solution of benzyl alcohol (internal standard) in 2% isopropanol/hexanes (HPLC grade). Samples were analysed using a Waters 2695 Alliance HPLC at a flow rate of 2.1 mL min$^{-1}$ (8.0% PrOH/hexanes) on a Sunfire Silica column (5 µm, 4.6×250 mm) and determined by their UV absorbance. The data are shown in FIGS. 2F and 2G.

Figure 3A:
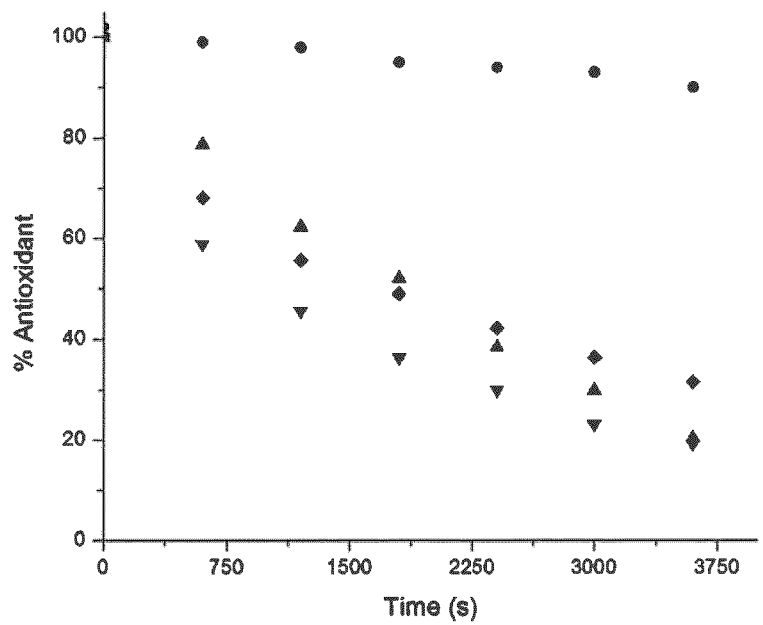
FIG. 3A. Decomposition of specified antioxidants at 160° C. under oxygen: 1 (▼), 2 (♦), 3 (▲) and 7 (●).
Figure 3B:
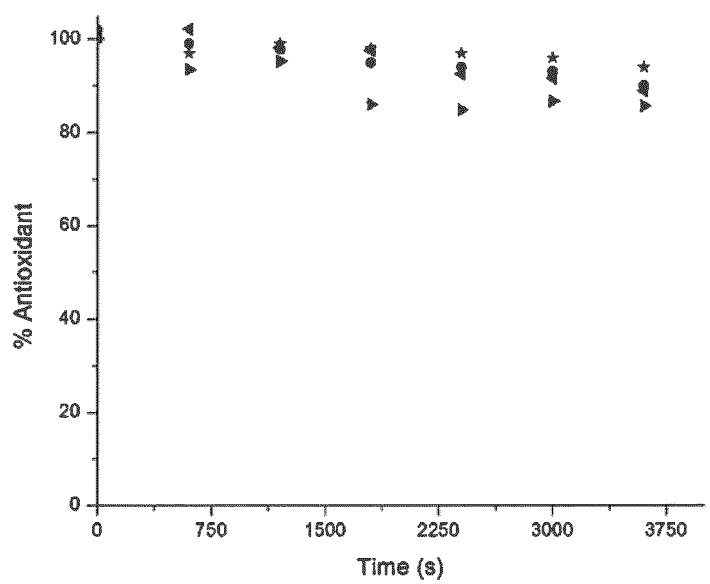
FIG. 3B. Decomposition of specified antioxidants at 160° C. under oxygen: 4 (◄), 5 (►), 6 (★) and 7 (●).

Example 4. Diarylamine Stability to Oxygen n-Hexadecane (100 mL) was thoroughly degassed with argon and then heated to 160° C. while argon was continuously bubbled through the liquid. Once the temperature stabilized, 2.5 mmol of diarylamines 1-7 were added to the solution and the flow of argon was replaced with O2. Aliquots (100 µL) were removed every 10 minutes, and added to 900 µL of a 2.2 mM solution of benzyl alcohol (internal standard) in 2% isopropanol/hexanes (HPLC grade). Samples were analysed using a Waters 2695 Alliance HPLC at a flow rate of 2.1 mL min$^{-1}$ (8.0% PrOH/hexanes) on a Sunfire Silica column (5 µm, 4.6×250 mm) and determined by their UV absorbance. The data are shown in FIGS. 3A and 3B.

Example 5. Determination of Carboxylic Acids in a Hexadecane Autoxidation

Figure 4A:
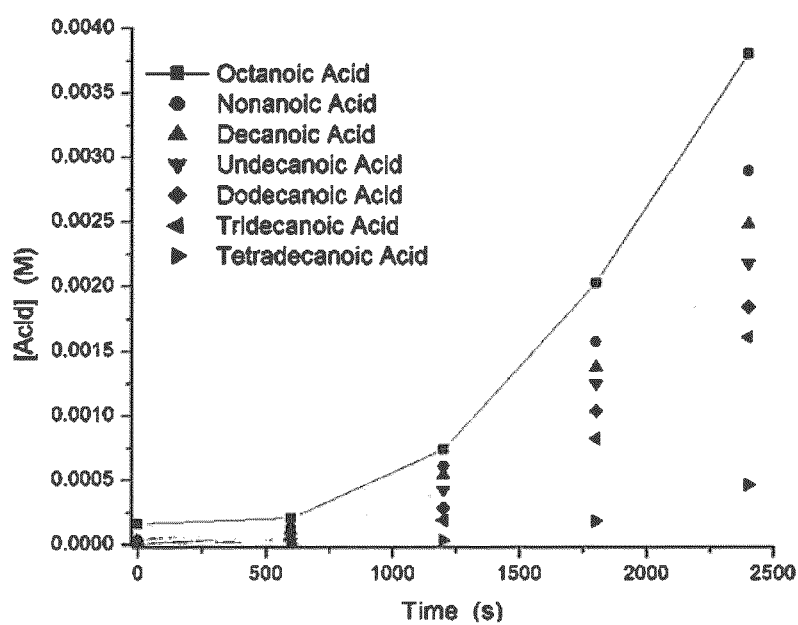
FIG. 4A shows the concentration of $C_8$ to $C_{14}$ carboxylic acids determined in the first 40 minutes of an uninhibited autoxidation of n-hexadecane at 160° C. initiated by 10 mM tetralin hydroperoxide.
Figure 4B:
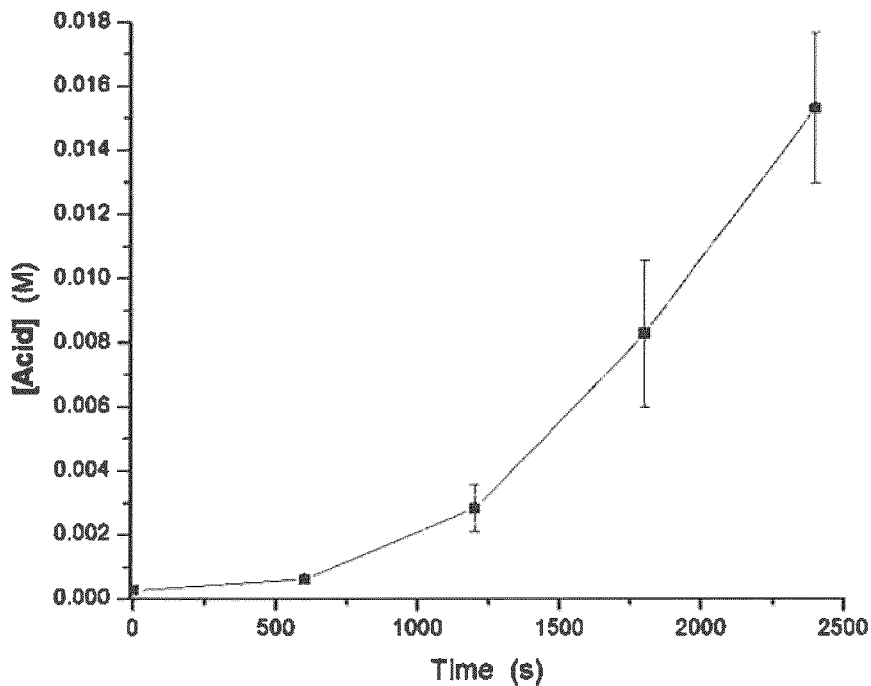
FIG. 4B graphically displays total carboxylic acid production during the autoxidation study described for FIG. 4A.

Aliquots (50 µL) were removed from uninhibited hexadecane autoxidations carried out as described above. The samples were diluted into 4.95 mL of a 20% iPrOH in MeOH solution containing 3,5-dimethylbenzoic acid (10.5 µM, internal standard). The samples were infused directly onto the TQ mass detector of a Waters Acuity H-Class UPLC-MS. The negative ion mass spectrum (from 50-400 m/z) of each sample was recorded three times, for 2 minutes per read, with a scan time of two seconds. Instrument parameters are as follows: capillary voltage=3.2 kV, cone voltage=40 V, extractor voltage=3V, source temperature=150° C., desolvation temperature=250° C., desolvation gas flow=500 L/hr, cone gas flow=50 L/hr. Standards were prepared from 2.0 mM solutions of octanoic, nonanoic, decanoic, undecanoic, dodecanoic, tridecanoic, and tetradecanoic acids (in the same hexadecane solution), and diluted in the same way as described above. Total acid concentration in an uninhibited hexadecane autoxidation is shown in FIG. 4B.

Example 6. PKA Measurements with Diarylamines 1-7

Figure 6A:
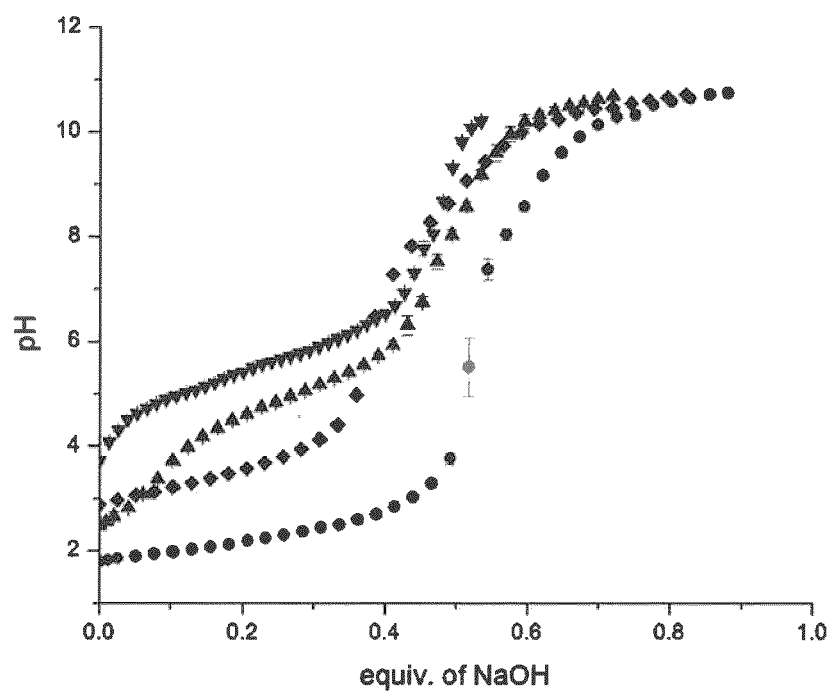
FIG. 6A displays titrations of solutions of diarylamines (1 mM) in 4:1 $CH_3CN:H_2O$ with 10 mM NaOH: 1 (▼), 2 (♦), 3 (▲) and 7 (●).
Figure 6B:
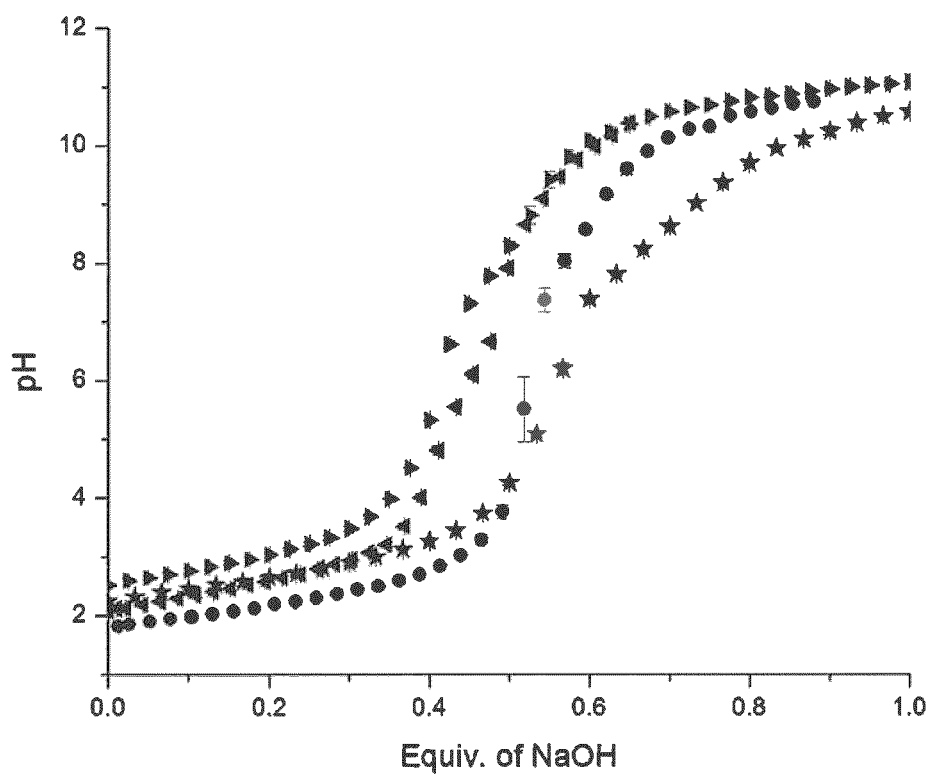
FIG. 6B displays titrations of solutions of diarylamines (1 mM) in 4:1 $CH_3CN:H_2O$ with 10 mM NaOH: 4 (◄), 5 (►), 6 (★) and 7 (●).

Solutions of the hydrochloride salts of diarylamines 1-7 (1 mM) were made up in 4:1 $CH_3CN:H_2O$ (3.0 mL) and the pH was measured using an Accument Electrode microbe referenced to Ag/Ag$^+$ as a function of added volumes of NaOH (10 mM). The $_s^s$pH in 4:1 (v:v) $CH_3CN/H_2O$ was obtained by adding 0.897 to the measured value as suggested in reference 2. The titration curves for the diarylamines are shown in FIGS. 6A and 6B (averages of triplicate experiments), and the pK$_a$s reported in the manuscript correspond to the pH when 0.5 molar equivalents of NaOH were added to the solution. Titration plots for diarylamines 1-7 are shown in FIGS. 6A-B.

Example 7. Peroxyl Radical Clock Kinetics with Diarylamine 5

Peroxyl radical clocking experiments (to determine the inhibition rate constant $k_{inh}$) for compound 5 were carried out according to our previously published reports (see Hanthorn, J., et al. *J. Org. Chem.* 2012, 77, 6895). Inhibition rate constants of the other compounds are as reported previously. A double reciprocal plot was used to obtain $k_m=2.4\times10^7$ $M^{-1}s^{-1}$ for compound 5.

Example 8. Electrochemical Studies with Diarylamine 5

A standard potential for diarylamine 5 was measured from its cyclic voltammagram obtained using a BASi potentiostat (available from BASi Analytical Instruments, West La Fayette, Ind., USA) with a glassy carbon working electrode, a platinum counter electrode and a Ag/AgNO3 reference electrode. The diarylamine was dissolved in degassed acetonitrile containing 0.1 M tetrabutylammonium hexafluorophosphate as supporting electrolyte and the current recorded in the range of 0-1 V at a scan rate of 200 mV/s. Standard potentials of the other compounds are reported in previous publications. A cyclic voltammogram of diarylamine 5 (1 mM in $CH_3CN$ containing 0.1 M $Bu_4NPF_6$) vs. $Ag/Ag^+$ gave $E^0=0.84$ V vs. NHE.

Example 9. General Procedure for Tetralin Autoxidation Experiment

Fresh tetralin was prepared by passing it through a column of silica. Tetralin (1.0 mL) was added to a glass vial, followed by chlorobenzene (1.0 mL). A magnetic Teflon-coated stir bar was added, and the vial was capped with a rubber septum. The vial was then placed in a heating block at 70° C. for 5 minutes. Antioxidant (4, 7) (0.002 mmol) were added. For those experiment where acid was present, as noted in the figure captions, hexanoic acid (0.050 mmol) was also added at this point. Azobis(α-tetralin) (0.1 mmol) was added as the initiator. The solution was stirred for 30 s and the first sample was taken. 100 μL samples were taken at regular intervals and added to 900 μL of a solution containing 2.2 mM benzyl alcohol, 10 mM butylated-hydroxytoluene, and 10 mM triphenylphosphine in 2% isopropanol/hexanes (HPLC grade). Samples were analysed using a Waters 2695 Alliance HPLC (2.0% iPrOH/hexanes, 1.6 ml $min^{-1}$; 10 min; Sunfire Silica column (5 μm, 4.6×250 mm)) and analysed by UV absorbance. See the results in graphs presented in FIGS. 18 and 19.

Example 10. THF in Aqueous Buffer Inhibited Co-Oxidations

THF/buffer autoxidations were carried out according to our previously published procedure (see Haidasz, E., et al. *J. Org. Chem.* 2016, Article ASAP. DOI 10.102¹/acs.joc.5b02183). Unstabilized THF (0.625 mL) was loaded into a 3 mL cuvette together with 100 mM phosphate buffer (1.8 mL) (adjusted to pH 4 and 7, as indicated in the figure captions). The cuvette was placed into the thermostated sample holder of a UV-vis spectrophotometer and allowed to equilibrate to 37° C. An aliquot (12.5 μL) of a 2.0 mM solution of Sty-BODIPY probe in DMSO was added, followed by 50 μL of 0.05 M solution of AAPH in $H_2O$, and the solution was thoroughly mixed. The absorbance at 562 nm was monitored for 10 min to ensure that the reaction was proceeding at a constant rate, after which 10 μL of a 600 μM solution of the test antioxidant was added. The solution was thoroughly mixed, and the absorbance readings were resumed. See results graphically displayed in FIGS. 20 to 25.

Buffer Recipe pH 4: 100 mM Acetate buffer: 1.24 g (15 mM) sodium acetate and 4.9 ml (85 mM) acetic acid were added to 1 L distilled water. The pH was measured using a pH meter and adjusted to pH=4.0 by addition of small amounts of 1M acetic acid or NaOH solutions in distilled water.

pH 7: 100 mM Phosphate buffer: 10.4 g (58 mM) potassium phosphate, dibasic and 5.75 g (42 mM) potassium phosphate, monobasic were added to 1 L distilled water. The pH was measured using a pH meter and adjusted to pH=7.0 by addition of small amounts of 1M HCl or NaOH solutions in distilled water.

All publications listed and cited herein are incorporated herein by reference in their entirety. It will be understood by those skilled in the art that this description is made with reference to certain preferred embodiments and that it is possible to make other embodiments employing the principles which fall within its spirit and scope as defined by the claims.

We claim:

1. A composition comprising a base and an antioxidant, wherein the base is 2,4,6-tri-tert-butylpyridine (TTBP), cesium carbonate, tert-alkylated primary amine, a metal oxide, metal hydroxide, or metal carbonate, wherein the metal of the metal oxide, metal hydroxide or metal carbonate is sodium, potassium, magnesium, calcium, or barium and the antioxidant comprises a compound of Formula II, or a salt thereof,

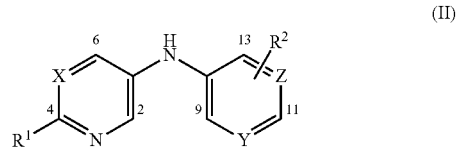

wherein each of X, Y, and Z are independently a carbon or nitrogen atom, and at least one of X, Y, or Z are nitrogen, wherein $R^1$ is an electron donating group, and $R^2$ is a hydrogen or an electron donating group bonded to a carbon atom in its aryl ring, wherein an electron donating group comprises a hydrocarbon group, an alkoxy group ($OR^3$), an amine group ($NH_2$), a monosubstituted amine ($NHR^4$) group, or a disubstituted amine ($NR^4R^5$) group, wherein $R^3$, $R^4$ and $R^5$ are independently hydrogen, saturated or unsaturated branched or straight chain hydrocarbon moiety, cycloaliphatic group, aromatic hydrocarbon, or a combination thereof, wherein the carbon atoms at positions 9 and 13 bear hydrogens, and wherein when $R^2$ is $OR^3$, $R^2$ is bonded to the carbon atom at position 11.

2. The composition of claim 1, wherein the electron donating group is an amine or a tert-butyl group.

3. The composition of claim 2, wherein the amine is a dialkylamine.

4. The composition of claim 1, wherein the compound of Formula II, is compound 1, 2, 4, 5, 6, 20, 22-23, 26, or any salt thereof

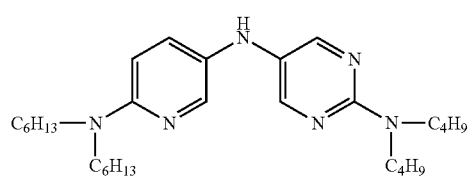

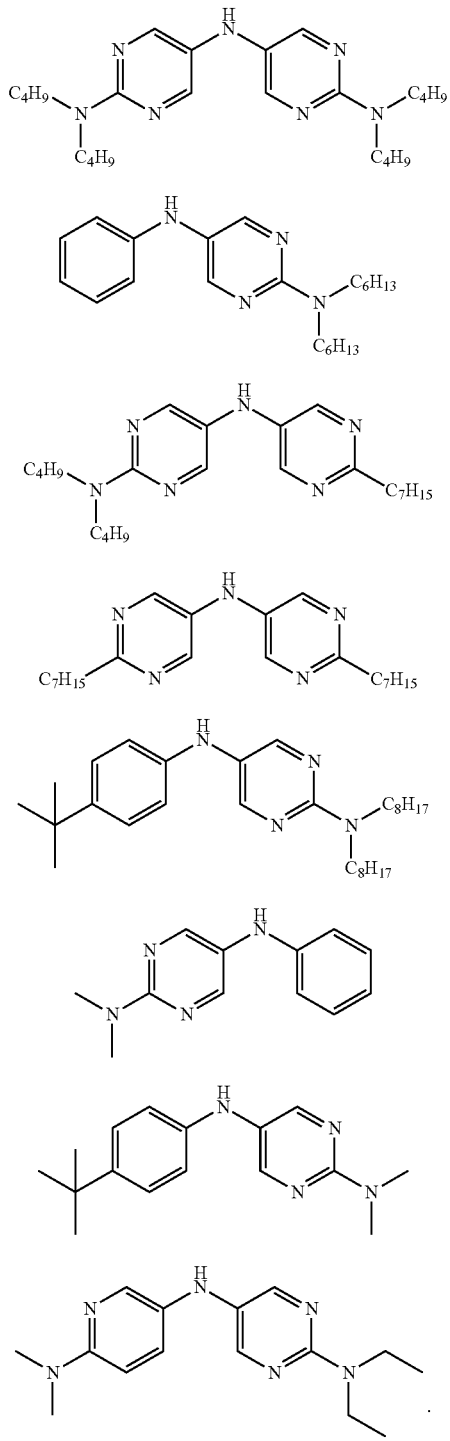

5. The composition according to claim 1, further comprising an organic substrate, wherein the organic substrate is a lubricant, biofuel, plastic, rubber, polymer, elastomer, cosmetic preparation, coating, dye, ink, pharmaceutical preparation, food preparation or adhesive.

6. The composition according to claim 1, further comprising an organic substrate, wherein the organic substrate is a lubricant, and the compound(s) are present in an amount of about 0.01 to about 6 weight percent of said lubricant.

7. The composition according to claim 1, wherein the composition further comprises one or more additional antioxidants.

8. The composition of claim 7, wherein the additional antioxidant is a sterically hindered phenol.

9. The composition according to claim 7, wherein the one or more additional antioxidants is selected from the group consisting of: traditional anti-oxidants, anti-wear agents, zinc salts, anti-deposition agents, hydrolytic stabilizers, friction modifiers, seal swell agents, anti-rust agents, foam suppressing agents, and pour point depressants.

10. A kit comprising a base selected from 2,4,6-tri-tert-butylpyridine (TTBP), cesium carbonate, tert-alkylated primary amine, a metal oxide, metal hydroxide, or metal carbonate, wherein the metal of the metal oxide, metal hydroxide or metal carbonate is sodium, potassium, magnesium, calcium, or barium and an antioxidant of Formula II, or any salt thereof,

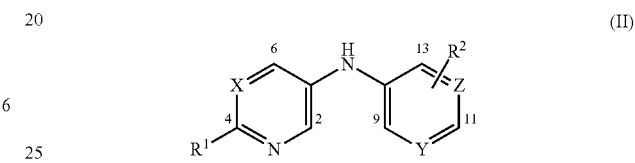

(II)

wherein each of X, Y, and Z are independently a carbon or nitrogen atom, and at least one of X, Y, or Z are nitrogen,
wherein $R^1$ is an electron donating group, and $R^2$ is a hydrogen or an electron donating group bonded to a carbon atom in its aryl ring,
wherein an electron donating group comprises a hydrocarbon group, an alkoxy group ($OR^3$), an amine group ($NH_2$), a monosubstituted amine ($NHR^4$) group, or a disubstituted amine ($NR^4R^5$) group,
wherein $R^3$, $R^4$ and $R^5$ are independently hydrogen, saturated or unsaturated branched or straight chain hydrocarbon moiety, cycloaliphatic group, aromatic hydrocarbon, or a combination thereof,
wherein the carbon atoms at positions 9 and 13 bear hydrogens, and
wherein when $R^2$ is $OR^3$, $R^2$ is bonded to the carbon atom at position 11, and
instructions to prevent or reduce degradation of the organic substrate by scavenging at least one free radical species from within a composition containing an organic substrate.

11. The kit of claim 10, wherein the compound of Formula II, is compound 1, 2, 4, 5, 6, 20, 22-23, 26, or any salt thereof

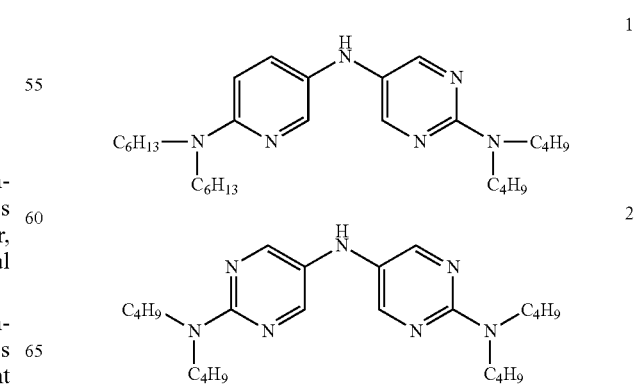

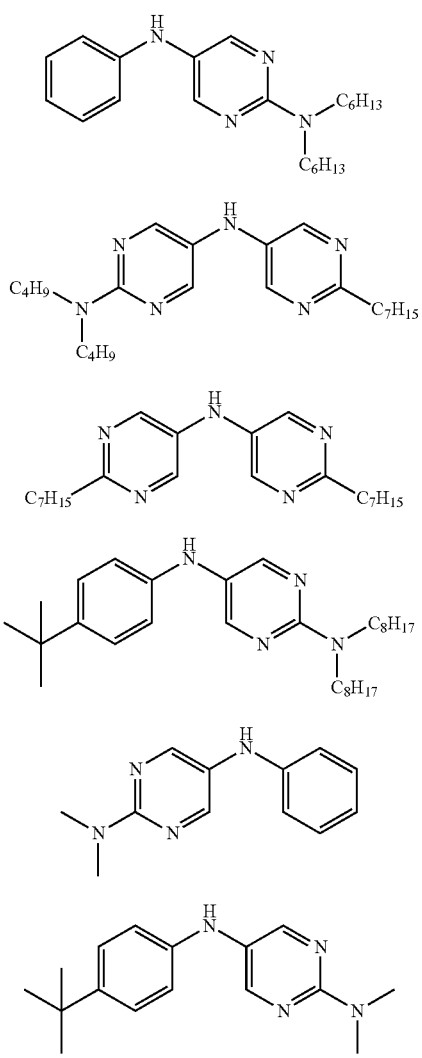

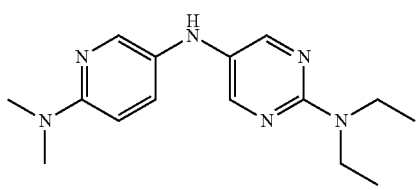

12. The composition of claim 1, further comprising an organic substrate,
    wherein the organic substrate is an engine oil, automatic transmission fluid, crank case lubricant, industrial utility grade oil, compressor oil, gear oil, hydraulic oil, biodiesel, plastic, rubber, rubber-like substance, unsaturated monomer, elastomer, adhesive, cosmetic preparation, coating, dye, ink, pharmaceutical preparation, or combustion engine lubricating oil.

13. The composition of claim 1, further comprising an organic substrate,
    wherein the organic substrate is an oil, fat, or wax used in the cosmetic and/or pharmaceutical industry, including those oils, fats or waxes that comprise esters of fatty acids, oil, fat, or wax used in manufacturing of food or food ingredients, almond oil, apricot oil, castor oil, corn oil, macadamia nut oil, olive oil, sesame oil, soybean oil, fish oil, bird oil, jojoba oil, bees wax, lanolin, oleic acid, linoleic acid, linolenic acid, or esters thereof.

14. A method of preventing or reducing the level of degradation of an organic substrate, the method comprising:
    adding to a composition that comprises an organic substrate, effective amounts of a composition of claim 1.

15. The method of claim 14, wherein the organic substrate is engine oil, automatic transmission fluid, crank case lubricant, industrial utility grade oil, compressor oil, gear oil, hydraulic oil, biodiesel, plastic, rubber, rubber-like substance, unsaturated monomer, elastomer, adhesive, cosmetic preparation, coating, dye, ink, pharmaceutical preparation, or combustion engine lubricating oil.

* * * * *